United States Patent
Kreher et al.

(10) Patent No.: US 10,590,153 B2
(45) Date of Patent: Mar. 17, 2020

(54) PROCESS FOR PRODUCING CRYSTALLINE DTPMP

(71) Applicant: Zschimmer & Schwarz Mohsdorf GmbH & Co. KG, Burgstädt (DE)

(72) Inventors: Thomas Kreher, Gröblitz (DE); Stephan Liebsch, Altenburg (DE); Carsten Rudolph, Frankenberg (DE)

(73) Assignee: Zschimmer & Schwarz Mohsdorf GmbH & Co. KG, Burgstädt (DE)

( * ) Notice: Subject to any disclaimer, the term of this patent is extended or adjusted under 35 U.S.C. 154(b) by 0 days.

(21) Appl. No.: 15/315,841

(22) PCT Filed: Jun. 2, 2015

(86) PCT No.: PCT/EP2015/062252
§ 371 (c)(1),
(2) Date: Dec. 2, 2016

(87) PCT Pub. No.: WO2015/185548
PCT Pub. Date: Dec. 10, 2015

(65) Prior Publication Data
US 2017/0101426 A1    Apr. 13, 2017

(30) Foreign Application Priority Data

Jun. 2, 2014    (DE) .................. 10 2014 210 377

(51) Int. Cl.
*C07F 9/38* (2006.01)
(52) U.S. Cl.
CPC .................. *C07F 9/3873* (2013.01)
(58) Field of Classification Search
None
See application file for complete search history.

(56) References Cited

U.S. PATENT DOCUMENTS

| | | |
|---|---|---|
| 4,477,390 A | 10/1984 | Ledent et al. |
| 5,495,042 A | 2/1996 | Belinka, Jr. et al. |

FOREIGN PATENT DOCUMENTS

| | | |
|---|---|---|
| DE | 690 27 828 T2 | 11/1996 |
| EP | 0 225 409 A1 | 6/1987 |

(Continued)

OTHER PUBLICATIONS

AVA Chemicals Private Limited Catalog Page disclosing Offer for Sale diethylene triamine penta (methylenephosphonic acid).

(Continued)

*Primary Examiner* — Clinton A Brooks
(74) *Attorney, Agent, or Firm* — FisherBroyles, LLP; Andrew K. Gonsalves, Esq.

(57) ABSTRACT

The present invention relates to crystallizates of the pure aminoalkylenephosphonic acid DTPMP in three crystal polymorphs and to a process for obtaining solid crystalline DTPMP by a preferably one-stage crystallization from an aqueous product mixture comprising DTPMP, wherein the process comprises the following process steps: (a) introducing seed crystals comprising DTPMP into an aqueous crude product comprising DTPMP with a total proportion in the range from 10 to 65 percent by mass up to a suspension density in the range from 1% to 25%; (b) introducing kinetic energy into the aqueous crude product to precipitate a crystallizate containing DTPMP as pure acid with a total content of at least 75% by mass; and (c) removing the crystallizate formed from the aqueous crude product by sedimentation and/or filtration, such that DTPMP is obtained as a solid end product in the form of a crystallizate.

11 Claims, 16 Drawing Sheets

(56) References Cited

FOREIGN PATENT DOCUMENTS

| EP | 0 411 941 A2 | 2/1991 |
| EP | 0 724 576 B1 | 3/2002 |
| EP | 1 838 720 B1 | 8/2010 |
| GB | 1 138 424 B | 4/1984 |
| JP | 2002105089 A | 9/2002 |
| RU | 2434875 C1 | 4/2010 |
| WO | 2010/136566 A1 | 12/2016 |

OTHER PUBLICATIONS

Huslenberg D., "Kristallisation," Georg Thieme Verlag KG published on ROMPP, an online German language technical encyclopedia, Publication date Jan. 9, 2017.
International Search Report for PCT/EP2015/062252 (International Priority Document for U.S. Appl. No. 15/315,841 dated Aug. 28, 2015).

PROCESS FOR PRODUCING CRYSTALLINE DTPMP

CROSS REFERENCE TO RELATED APPLICATIONS

This application is a U.S. National Phase filing under 35 U.S.C. § 371 of International Application No. PCT/EP2015/062252, filed Jun. 2, 2015, and published as WO 2015/185548-A1 on Dec. 10, 2015, which claims priority to German Patent Application No. DE 10 2014 210 377.0, filed Jun. 2, 2014, the entire disclosures of which are hereby incorporated herein by reference.

FIELD OF THE INVENTION

The present invention relates to crystallisates of the pure aminoalkylenephosphonic acid DTPMP in three crystal modifications, and to a process for obtaining solid crystalline DTPMP by a preferably one-step crystallisation from an aqueous product mixture containing DTPMP.

BACKGROUND OF THE INVENTION

For many decades, aminoalkylenephosphonic acids have been used worldwide at a rate of about 100,000 tonnes of active substance molecule per year. The main fields of use are the detergents and cleaning agents industry and a wide variety of water treatment technologies in which aminoalkylenephosphonic acids and their salts act as multifunctional additives.

Owing to their production, aminoalkylenephosphonic acids are for the most part marketed as aqueous solutions. The solid aminoalkylenephosphonic acids necessary for special applications, for example for use in formulations in powder, lump or paste form, must be produced from the aqueous synthesis solutions in additional process steps. The group of the aminoalkylenephosphonic acids includes a large number of liquid products based on diethylenetriamine penta(methylenephosphonic acid) (DTPMP), which crystallises from aqueous solutions only with difficulty.

The reason for this is the very good complexing power for a large number of metal ions, an excellent stabilisation of water hardness, coupled with a pronounced ability to disperse solid particles and protection of metal surfaces against corrosion. This results in the very wide variety of fields of application of DTPMP, such as, for example, in washing and cleaning processes and as a chelate former in the stabilisation of peroxide bleaches and as an additive for the treatment of drinking water, water for industrial use and oil field water treatment.

Accordingly, there is a great need for DTPMP products which are preferably free of accompanying ions and discolourations and which can be supplied not only as aqueous solutions but also as solids, in order thus to open up a large number of new possible uses to the formulator.

Processes for the production of DTPMP are known and disclosed in detail, for example, in DE 3128755 A1 or EP 1 838 720 B1. However, the products based on DTPMP which are available commercially at present have only inadequate purities and are present only as aqueous products.

DTPMP is obtainable commercially exclusively in aqueous solutions. However, the aqueous products currently offered on the market are not free of accompanying ions and comprise significant amounts of impurities, so that they always have a brownish colour and, in addition, a pronounced characteristic odour. This limits the practical usability of aminoalkylenephosphonic acid, which, from the point of view of application, is extraordinarily flexible.

In this connection there is known, for example from U.S. Pat. No. 4,477,390 A, an exclusively aqueous DTPMP concentrate which is stable to storage at room temperature, wherein the DTPMP is to be kept in solution only in admixture with its lesser substituted representatives (D3A and D4A) and by the addition of high concentrations of at least from 18 to 22 percent by weight of non-oxidising mineral acids (for example HCl).

A large number of attempts are to be found in the literature to improve the product qualities of aqueous solutions of aminoalkylenephosphonic acids or to increase the variety of products. In addition to a wide range of variants for optimising the synthesis, attempts at subsequent purification and the technical production of solids are known.

EP 0411941 B1 discloses in this connection a chemical separation process for the purification of aminomethylenephosphonic acids using an acid-base reaction. After the aminoalkylenephosphonic acid in question has been dissolved in an aqueous base, the aminoalkylenephosphonic acid is recrystallised by the stepwise addition of an acid. The resulting precipitate is then filtered and washed with water. In EP 0411941 B1 it is explicitly mentioned that the claimed process is not suitable for the purification of DTPMP.

EP 724576 B1 discloses a process for the non-alkaline purification of aminoalkylenephosphonic acids. In this process, the crude products, after being suspended in water, are heated to reflux at a neutral or acidic pH. Following the heat treatment, the precipitate is filtered and washed with water. The described process is suitable, for example, for the purification of EDTMP and DOTMP. Because the solubility of DTPMP increases sharply at elevated temperatures of from 60 to 70° C., the process is not suitable for suspending DTPMP in water in order to isolate it under reflux conditions. Recrystallisation by cooling the solution therefore also does not lead to industrially usable amounts.

Typical, commercially available pH-acidic DTPMP products are obtainable exclusively as liquid products because, owing to the impurities they contain as a result of their synthesis, pH-acidic DTPMP solids cannot be manufactured in a storage-stable manner without the aid of stabilisers. Stabilisation of pH-acidic DTPMP liquid products against uncontrolled precipitations is essential. This is effected either by partial neutralisation, at least the trisodium salt or by addition of foreign acids (for example at least 10% by mass HCl).

Granulated sodium salts of DTPMP contain additives from their production, so that the fraction of DTPMP in those solids is significantly less than 40% by mass.

Conventional drying methods such as spray drying or granulation either lead to extremely hygroscopic powders or use technologies in which the active ingredient content of the poorly drying aminoalkylenephosphonic acid DTPMP is lowered by additives, which in turn limits the scope of application of the dry substance. Solid DTPMP products have thus hitherto been unable to establish themselves on the market, as is the case, for example, with the widely used powdered and granular products of the hydroxybisphosphonic acid HEDP.

Since the processes described above for purifying aminoalkylenephosphonic acids containing large amounts of accompanying substances and impurities are not suitable for technical, economic or ecological reasons for purifying and obtaining solid DTPMP, there is therefore a great need for such a process.

DETAILED DESCRIPTION OF THE INVENTION

Accordingly, the object of the invention is to provide a process for purifying and obtaining solid pure aminoalkylenephosphonic acid DTPMP.

According to the invention, the object is achieved by a process for obtaining solid crystalline DTPMP as a pure acid of the general formula (I) from an aqueous crude product containing DTPMP and having a pH of less than 4, preferably less than 3 (called aqueous crude product in the following), comprising the following steps:
  a. introducing seed crystals containing DTPMP into an aqueous crude product containing DTPMP with a total fraction in the range of from 10 to 65% by mass, up to a suspension density in the range of from 1 to 25%,
  b. inputting kinetic energy into the aqueous crude product, for example by intensive stirring and/or shaking and/or inputting vibrations, whereby a crystal layer grows starting from the seed crystals, so that a crystallisate of the general formula (I) containing DTPMP as the pure acid in a total content of at least 75% by mass is formed and precipitates,
  c. separating the crystallisate that has formed from the aqueous crude product by sedimentation and/or filtration,
wherein the crystallisate of the pure acid DTPMP has the general formula (I):

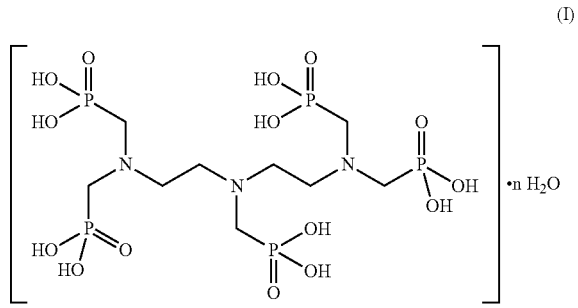

(I)

wherein n is a number between 0 and 2.

The process according to the invention has the advantage that DTPMP, as an aminoalkylenephosphonic acid which has a high supersaturation tendency and at the same time a low nucleation rate and crystal growth rate and therefore can be crystallised from aqueous solutions only with difficulty, is obtained as a solid end product in the form of a crystallisate by a preferably quasi-continuous process. Advantageously, undesirable impurities are separated off by the process, preferably during the crystallisation of DTPMP, so that the crystallisate has a high degree of purity. Most advantageously, crystallisates containing DTPMP which are obtained by the process according to the invention have a substantially lower hygroscopy compared with solids comprising DTPMP obtained by means of conventional methods.

Most advantageously, the aminoalkylenephosphonic acid is obtained as a solid in the form of a crystallisate by complete crystallisation without inorganic or organic impurities, such as, for example, cytotoxic lead impurities and secondary products resulting from the synthesis and unreacted raw materials.

Further advantageously, high degrees of purity are achieved by the process, which satisfy requirements that are made for applications in the detergents and cleaning agents industry, such as low toxicity, no corrosivity, loss of colour due to impurities, and the high demands in terms of purity which are made of chemicals for the electronics industry and metal treatment.

Fortunately, it has additionally been shown that the process according to the invention is more economical and more environmentally friendly than conventional methods for obtaining solid aminoalkylenephosphonic acids, because it is advantageously possible to dispense with the use of other chemicals or expensive subsequent process steps.

The present invention is based on the recent finding that the solubility of the aminoalkylenephosphonic acid DTPMP and its tendency to supersaturation fall as the degree of purification increases (that is to say as the fraction of impurities falls).

It is already known to the skilled person from U.S. Pat. No. 4,477,390 A (Monsanto Company, 16, Oct. 1984; columns 5 and 6, examples 1 to 34) that the solubility of DTPMP is increased by the addition of high concentrations of accompanying ions (for example HCl, $H_2SO_4$). According to the teaching of the patent specification, the concentration of added HCl should be at least 15 percent by weight in order to provide an aqueous DTPMP concentrate which is stable to storage (that is to say without the input of kinetic energy) and contains up to 40 percent by weight phosphonate. By the combined use of a plurality of accompanying ions, for example HCl and $H_2SO_4$, it is even possible to obtain liquid DTPMP products with up to 60% DTPMP in solution.

Owing to its synthesis, the aqueous crude product of DTPMP usually contains residual amounts of chloride ions, for example after its preparation with HCl as acid catalyst (up to 18% by mass). Surprisingly, however, it has now been found that chloride ions at relatively low concentrations in the range of from 1 to 4% by mass lead to a further reduction in solubility and/or reduction in the supersaturation tendency of DTPMP (cf. FIG. 13).

Suspensions (also called slurry in the following, that is to say a heterogeneous mixture of solid particles, containing DTPMP, and the aqueous crude product) from preparation processes in which alternative acid catalysts to HCl are used, for example methanesulfonic acid (up to 25%) or sulfuric acid (up to 25%), also show a comparable solubility behaviour.

It is assumed that with equimolar substance amount ratios in solution a salt formation takes place via at least one nitrogen atom of the aminoalkylenephosphonic acid DTPMP (for example DTPMP hydrochloride DTPMP*HCl), as a result of which the steric mobility of the DTPMP molecules is limited, so that the solubility is lowered. It is all the more surprising that the free aminoalkylenephosphonic acid and not the salt thereof DTPMP*HCl nevertheless crystallises. The purification effect is accordingly advantageously not hindered. This behaviour can be used particularly advantageously to increase the yield of crystallisate by deliberately leaving residual amounts of mineral acid (for example from 1 to 5% by mass chloride ions) in the DTPMP slurry or adding them thereto, which is comparable to the chloride contents of DTPMP products which are customary on the market (substance amount ratio of a typical DTPMP slurry due to the synthesis).

By definition, the solubility of a substance is to be understood as meaning the maximum amount of a substance which is homogeneously distributed in a solvent without the substance being present as a solid phase (solid) as a result of a crystallisation. The solubility indicates how many grams (g) of the substance in its pure form can be dissolved in 100 g of solvent.

However, when a saturated solution of the aminoalkylenephosphonic acid DTPMP is slowly cooled, the onset of crystallisation, which leads to the formation of a solid phase of DTPMP, can easily be passed over, so that crystallisation does not occur to the extent necessary to ensure thermodynamic equilibrium and also takes place with a time delay. The rate of crystallisation and nucleation rate of DTPMP are very low, for which reason, even when a small amount of solid particles (0.1-2.0% by mass) containing DTPMP is introduced (that is to say seeded) into a saturated solution and then incubated (that is to say without the input of kinetic energy), no appreciable amounts of DTPMP are precipitated as a solid even after days, weeks or months. Only the active sites of the added solid particles are saturated, and the further crystallisation process comes to a halt.

By definition, exceeding the maximum soluble amount of a substance, which does not lead to crystallisation by the time the equilibrium state is reached, is referred to as supersaturation. A supersaturated solution is accordingly in a metastable state, wherein no or only slight crystallisation takes place.

Particularly advantageously, undesirable accompanying substances and impurities are separated from the aminoalkylenephosphonic acid DTPMP by the process according to the invention, because they either remain undissolved from the outset and can thus readily be separated from an aqueous crude product even before the process according to the invention, or because, even if they do go into solution, they remain in the aqueous crude product on account of their low concentration when the crystallisate has already precipitated.

Further developments, advantages and possible applications of the invention will also become apparent from the following description. All the described features, on their own or in any desired combination, form the subject matter of the invention, regardless of their aggregation in the claims or their appendancies.

The starting point of the process according to the invention is a crude product, containing at least DTPMP, which is present as a dry substance, in dissolved form and/or as a suspension, preferably in water. The crude product preferably contains DTPMP in a concentration of at least 5% by mass, preferably from 10 to 90% by mass, more preferably from 20 to 80% by mass.

The data in percent by mass (m %) are derived from the mass fraction w of the constituent in question in the (aqueous) solution and are given as the hundredfold of that value (m %=100*w). The mass fraction of the constituent in question is determined as the fraction of the mass of that constituent in the mass of the total solution after mixing, that is to say the masses of all the constituents dissolved in the solvent plus the mass of the solvent itself.

Within the meaning of the invention, the expression "aqueous crude product" means that the crude product to be purified is homogeneously dissolved and/or suspended preferably in water or a water-containing solution at the beginning of the purification process according to the invention. The aqueous crude product can contain, in addition to DTPMP, impurities in the form of secondary products and/or unreacted educts. Secondary products are inorganic secondary products such as, for example, phosphates and organic secondary products. Unreacted educts are, for example, chlorides and phosphorous acid ($H_3PO_3$).

The organic secondary products can be divided into lesser substituted products and condensation products. Lesser substituted products form in the incomplete reaction of the primary or secondary amine (for example with formaldehyde and phosphorous acid $H_3PO_3$), wherein some N—H functionalities are retained or N—$CH_3$ functionalites are formed.

Condensation products can form between $H_3PO_3$ and the formaldehyde and are, for example, hydroxymethanephosphonic acid.

Educts such as formaldehyde or $H_3PO_3$ can additionally be present in a concentration of from 0 to 15% by mass. Phosphoric acid $H_3PO_4$ which is likewise present forms by oxidation of phosphorous acid $H_3PO_3$ as a secondary reaction. Owing to the synthesis, an aqueous crude product contains acids, for example HCl, $H_2SO_4$, $H_3PO_3$, $H_3PO_4$ and/or methanesulfonic acid, in a total concentration, based on DTPMP, of from 0 to 30% by mass.

In one embodiment according to the invention, the aqueous crude product contains, in addition to DTPMP, impurity in the form of secondary products and/or unreacted educts.

The crude product can contain lesser substituted DTPMP derivatives in a concentration of from 0 to 15% by mass, preferably from 0.1 to 10% by mass, and/or other secondary products (for example phosphoric acid, hydroxymethanephosphonic acid and others), which have been formed in the case of an incomplete conversion of the chemical reaction. In the case of an incomplete synthesis, the crude product can additionally contain residues of unreacted starting materials (for example formaldehyde, hydrochloric acid, phosphorous acid and others) in a concentration of from 0 to 15% by mass, preferably from 0.1 to 10% by mass.

The advantage of the process according to the invention lies in the selective separation of the DTPMP from the mentioned impurities. Although the inorganic secondary products can be separated off by known methods of precipitation with solvents, the organic secondary products, which are of similar molecular structure and comparable solubility, cannot be separated off completely by such methods.

The aqueous crude product preferably contains DTPMP with a total fraction in the range of from 10 to 65% by mass, more preferably from 15 to 65% by mass, most preferably in the range of from 20 to 60% by mass.

The mass fraction of a constituent (for example of an aminoalkylenephosphonic acid) in solution can be determined by various ways known to the skilled person, for example by gravimetric methods, by complexometric titration or by acid-base titration.

An aqueous crude product to be purified can suitably be prepared preferably analogously to the works of Moedritzer and Irani (*J. Org. Chem.* 1966, 31, 1603-1607). In the presence of a strong acid (for example hydrochloric acid (HCl), sulfuric acid), preferably primary amines (for example ammonia, aminoethane, 1,2-diaminoethane, aminoethanol, etc.), phosphorous acid ($H_3PO_3$) and formaldehyde are reacted to phosphonic acids, having regard to the stoichiometric ratios necessary for a possible conversion which is as complete as possible of all the N—H functionalities. As an alternative to the use of $H_3PO_3$ and HCl, it is also possible to work with phosphorus trichloride and water. In the case of a phosphonomethylation carried out in such a manner, the fully substituted aminoalkylenephosphonic acid as the main product is usually obtained with a purity of from 75 to 85%.

Alternatively, an aqueous crude product containing DTPMP can also be obtained, for example, via a nucleophilic substitution reaction based on a Michaelis-Arbuzov reaction (Berichte 1898, 31, 1048) with subsequent acid hydrolysis.

There can preferably be used as the aqueous crude product also commercial aqueous solutions containing DTPMP in a total amount of from 20 to 60% by mass, which are marketed, for example, under trade names such as, for example, CUBLEN® DNC 450, CUBLEN® D5000 of Zschimmer & Schwarz, as well as partially neutralised and neutralised commercial products in the form of the sodium salt, such as, for example, Cublen D 5113 (pH 2-3), Cublen D 4217 (pH 6-8).

Alternatively, a water-containing crude product can preferably be prepared by dissolving and/or suspending a solid comprising DTPMP in water or a water-containing solution. The solid is preferably dissolved and/or suspended in one or more aqueous solvents with heating to a temperature of more than 30° C., more preferably to a temperature of from 30 to 100° C., most preferably from 35 to 60° C.

A fraction of undesirable impurities advantageously remains undissolved during the operation of dissolving the DTPMP and can thus be separated from the water-containing crude product by filtration and/or sedimentation even before the crystallisation process.

Preferably, an aqueous crude product has a pH of less than 5, preferably less than 4, most preferably less than 3. The pH range of the water-containing crude product can optionally be adjusted by adding an acid (for example hydrohalic acid, $H_3PO_4$) and/or a base (for example alkali, alkaline earth lye). Methods for determining the pH are very well known to the skilled person.

The mass fraction of a constituent (for example of an aminoalkylenephosphonic acid) in solution can be determined by various ways known to the skilled person, for example by gravimetric methods, by complexometric titration or by acid-base titration.

According to the invention, a seed crystal is a particulate solid which, as substrate, induces the crystallisation and maturation of the crystallisates and thus serves as the matrix material for the growth of the crystal layer for obtaining a solid (that is to say crystallisation) containing DTPMP, so that the crystallisate is formed. Seeding accordingly means the introduction of seed crystals into a solution in order to initiate crystallisation after the saturation concentration has been exceeded. These seed crystals preferably consist of type-specific crystallisate, that is to say crystals or fragments of crystals which have been obtained beforehand under comparable conditions.

A seed crystal is preferably a type-specific crystalline solid which contains DTPMP in a mass fraction, based on the seed crystal, of from 50 to 100% by mass, more preferably from 70 to 100% by mass, most preferably from 75 to 95% by mass. Within the meaning of the invention, a mass fraction of a component of 100% by mass means that the fraction of other components is below the detection limit. The seed crystal is preferably type-specific and has a high specific surface area. The seed crystals preferably have an edge length in the range of from 0.1 to 100 μm, more preferably from 0.5 to 50 μm.

It can be of particular importance that in this context the seed crystals produced in the precrystallisation step are present in a desired stable type-specific crystal modification. For the process according to the invention, these are the α, β and γ crystal modifications of pure DTPMP.

By introducing seed crystals into the aqueous crude product, a suspension (also slurry, that is to say a heterogeneous mixture of solid particles, containing DTPMP, and the aqueous crude product) is formed. The aqueous crude product thereby serves as the carrier liquid in which the solid particles are present in coarsely dispersed form and therefore tend to sediment.

The crystallisation is advantageously accelerated by the high specific surface area of the added solid particles. Crystallisation means herein the growth of ions, molecules or ion and molecule aggregates, containing DTPMP, from the aqueous solution at the contact surface of the seed crystal and/or the crystallisate by adsorption.

Through a specified high specific surface area in the form of added solid particles, the almost non-existent tendency of DTPMP to self-nucleation and the extremely low crystallisation rate are circumvented.

It is known in principle to the skilled person that he can initiate the crystallisation of common aminoalkylenephosphonic acids by introducing very small amounts (suspension density less than 0.5% by mass) of seed crystals, whereby orderly crystal growth can be achieved up to or almost up to the equilibrium point, that is to say with only very slight residual supersaturation, with only very small amounts. By contrast, the inventors have now found, surprisingly, that this is not the case for the aminoalkylenephosphonic acid DTPMP. Instead, substantially larger seed amounts are required for the orderly crystallisation of DTPMP close to the equilibrium point.

Advantageously, the amount of seed crystals introduced into the aqueous crude product allows the period until transition to steady-state operation to be accelerated. The aqueous crude product is preferably contacted with a seed crystal amount in the form of seed crystals, containing DTPMP, up to a suspension density of from 0.1 to 25% by mass, more preferably from 0.2 to 20% by mass, most preferably from 1 to 20%.

According to a preferred embodiment of the present invention, seed crystal amounts with a suspension density of from 1 to 25% by mass, more preferably from 5 to 20% by mass, most preferably from 10 to 20%, have been found to be particularly suitable.

A suspension is a heterogeneous mixture of solid particles of the seed crystals and/or of the crystallisate in water or an aqueous solution. The water or an aqueous solution serves as the carrier liquid in which the solid particles of the seed crystals and/or of the crystallisate are present in coarsely dispersed or finely dispersed, preferably finely dispersed, form.

In order to ensure that a suspension of solid particles (that is to say seed crystals and/or crystallisates) in a carrier liquid is flowable and pumpable, the suspension density of a suspension of seed crystals and/or crystallisates in an aqueous solution is preferably not more than 70%, more preferably not more than 60%, most preferably in the range of from 20 to 55%. The suspension density is a measure of the solids content in a suspension and is defined as the proportion of suspended solid particles in kg per $m^3$ of carrier liquid (%).

For obtaining a solid (precipitating the crystallisate), the aqueous crude product preferably has a temperature in the range of from 0 to 85° C., more preferably from 15 to 80° C., most preferably from 25 to 75° C., since the solubility of DTPMP in the water-containing crude product is disadvantageously too high above 85° C.

The aqueous crude product is preferably set in motion by inputting kinetic energy during and after the introduction of seed crystals, so that the seed crystals and/or crystallisates are kept suspended in the aqueous suspension. The input of kinetic energy advantageously effects intensive and complete mixing of the aqueous crude product and the seed crystals which are optionally present in the reaction chamber, so that homogeneous distribution of the components and constant material transport in the aqueous solution are ensured.

Material transport means herein that, by the diffusion of individual ions, molecules or ion and molecule aggregates, containing DTPMP, from the aqueous solution at the contact surface of the seed crystals and/or of the crystallisate, the growth of the crystallisates by adsorption is accelerated.

Advantageously, after diffusion of the ions, molecules or ion and molecule aggregates, containing DTPMP, at the contact surface of the seed crystal and/or of the crystallisate and adsorption thereof at the contact surface, surface diffusion of the precursors takes place, which facilitates the operation of controlled crystallisation of the solid particles containing DTPMP.

It is generally known to the skilled person that the input of kinetic energy is not required for crystallisation, that is to say the system is at rest.

Surprisingly, it has now been shown that the formation of the crystallisate, in particular the growth of the crystal layer by adsorption, is facilitated by the presence of seed crystals and/or crystallisates which have fractured edges which differ from the ideal crystal forms. The input of kinetic energy thereby advantageously effects mechanical breaking at the surface of the seed crystal and/or of the crystallisate, whereby secondary nucleation takes place. As a result of the mechanical breaking at the surface of the seed crystal and/or of the crystallisates, new active sites are advantageously constantly formed, which are saturated by the constant diffusion and adsorption of individual ions, molecules or ion and molecule aggregates, containing DTPMP, from the aqueous solution at the contact surface of the seed crystal and/or of the crystallisate. The input of kinetic energy is consequently essential for carrying out the process according to the invention.

According to a preferred embodiment of the present invention, the input of kinetic energy is advantageously carried out in such a manner that mechanical breaking takes place at the surface of the seed crystal and/or of the crystallisate and secondary nuclei are formed, the Reynolds number of the stirring members preferably being above Re (stirring)=10, more preferably in a characteristic number range of from 50 to 4000.

The effect of the mechanical breaking of seed crystals and/or crystallisates which have been introduced can additionally be increased in a beneficial manner by increasing the suspension density and/or modifying the stirrer geometry. The probability of effective collisions between the seed crystals and/or crystallisates is advantageously increased thereby.

The process of crystallisation in the form of the growth of a crystal layer on the seed crystal or the crystallisate can be monitored, for example, by microscopic, electron microscopic, thermogravimetric analysis methods and laser diffraction. The composition of the crystalline solids can be determined, for example, by means of high-resolution nuclear magnetic resonance spectroscopy (NMR) or X-ray diffraction. The active content of DTPMP in the aqueous crude product is determined, for example, by means of complexometric titration or acid-base titration. Contents of other constituents, such as chloride ions and phosphorus-containing impurities, can be determined, for example, by argentometric and/or iodometric titration, capillary electrophoresis or by spectrophotometry.

According to a preferred embodiment of the process according to the invention, the input of kinetic energy into the system is carried out by stirring and/or shaking and/or ultrasound treatment, in order advantageously to ensure intensive mixing of the system.

The speeds during stirring and/or shaking are preferably infinitely variable in order to allow the desired stirring or shaking movement to be adjusted optimally. The input of kinetic energy advantageously increases material transport, which is highly diffusion-controlled, during the formation of the crystallisate. Diffusion-controlled material transport here means that, by the diffusion of individual ions, molecules or ion and molecule aggregates, containing DTPMP, from a solution at the contact surface of the seed crystals or crystallisates, orderly growth thereof and the formation of crystalline structures is accelerated.

According to the invention, the term crystallisate is understood as meaning a preferably particulate, crystalline solid which in dried form contains the DTPMP as the pure acid with a total fraction of more than 75% by mass, preferably more than 80% by mass, more preferably at least 85% by mass, for example determined using an NMR spectrometer, by capillary electrophoresis or by means of complexometric titration. A crystallisate preferably has an edge length in the range of from 20 to 1000 µm, more preferably from 30 to 500 µm, most preferably from 30 to 200 µm.

The crystallisates obtained following the process according to the invention are obtained as lance-shaped, plate-like or cuboid crystals, containing DTPMP as the pure acid.

A crystallisate preferably comprises impurities (as described above) only with a total fraction of less than 1.0% by mass, more preferably less than 0.5% by mass, but most preferably less than 0.3% by mass. However, the skilled person knows that individual impurities with a fraction below the detection limit may be present.

A crystallisate preferably comprises the aminoalkylenephosphonic acid DTPMP in the form of the crystalline anhydrate (that is to say the pure acid DTPMP in which all the phosphonic acid groups are protonated), of the mono- or di-hydrate of the acid DTPMP, more preferably in the form of the monohydrate of the acid DTPMP.

Within the meaning of the invention, the term "monohydrate" or "dihydrate" denotes a crystallisate of the free acid DTPMP, wherein the crystallisate is in the form of a solid addition compound ("solvate") in which one or two water molecules ("water of crystallisation") are attached to a molecule of the acid DTPMP, so that the water molecules form part of the crystal structure of the crystallisate. The term "anhydrate", however, denotes a crystallisate of the acid DTPMP that is free of water of crystallisation, free of water of crystallisation meaning that, mathematically (based on one crystallisate), less than 0.4, preferably less than 0.3, more preferably less than 0.2 water molecules are attached to a molecule of the acid DTPMP. Stoichiometrically, the monohydrate contains 3% by mass water in the crystallisate and the dihydrate contains 5.9% by mass water in the crystallisate.

By definition, retained water refers to the sum of capillary water and adsorbed water. Adsorbed water refers to water which has accumulated on the surface of crystallisates, a film of water molecules forming. Capillary water refers to the amount of water which is retained in the capillaries of a solid (pore diameter to a maximum of 0.2 µm) by adhesion and cohesion (which corresponds to tension). The skilled person knows that the amount of water which forms a surface film or fills the capillaries varies in dependence on the ambient parameters (for example temperature, pressure, water tension).

Methods for the chemical analysis of solids are very well known to the skilled person and are based, for example, on thermal analysis (DTA/TG). Methods of structural analysis are also known to the skilled person and are based, for example, on X-ray crystal structure analyses (for example powder diffraction, single-crystal structure analysis) or the evaluation of epitactic effects.

According to a preferred embodiment of the present invention, the crystallisates obtained by the process according to the invention are plate-like or quadratic and have an aspect ratio (length to width) in the range of from 1:1 to 10:1.

According to an alternative embodiment of the present invention, the crystallisates obtained by the process according to the invention are preferably lance-shaped and have an aspect ratio of at least 3:1.

According to a preferred embodiment of the process according to the invention, the seed crystal is a comminuted crystallisate, with identical composition thereto.

The crystallisate is separated from the aqueous crude product preferably by sedimentation (for example by centrifugation) and/or by filtration (for example using a Büchner funnel). According to a particularly preferred embodiment of the invention, the crystallisate is separated from the aqueous crude product by filtering centrifugation so that residues of mother liquor (that is to say of the aqueous crude product) are advantageously separated from the crystallisate and the surface thereof by the combination of centrifugal force and filtration.

It can optionally be provided that the separated crystallisate is washed repeatedly after separation with cold, distilled water and/or with a water-containing solution containing, for example, from 5 to 20% by mass ethanol or from 5 to 10% by mass hydrochloric acid. In particular by repeated washing with a water-containing solution containing, for example, from 5 to 20% by mass ethanol, a loss of separated crystallisate due to washing is reduced because the pure acid DTPMP is only sparingly soluble therein.

After separation of the crystallisate from the water-containing crude product, the separated crystallisate is in the form of a crystalline solid comprising DTPMP as the pure acid, wherein the separated crystallisate contains DTPMP with a content of dry matter of at least 75% by mass, preferably more than 80% by mass, more preferably from 85% by mass to 99% by mass.

According to a preferred embodiment of the present invention, the process comprises at least one isothermal process stage in which the conditions for obtaining solid crystalline DTPMP are so chosen that the temperature difference in the aqueous crude product is constant, that is to say not more than 2.5 K, preferably not more than 2 K, more preferably not more than 1 K, over a defined period of the input of kinetic energy. This precise isothermal procedure advantageously yields crystallisates having a high degree of purity.

Alternatively, crystal growth and nucleation can be stimulated by pulsed temperature application.

According to a preferred embodiment of the process according to the invention, the temperature of the aqueous crude product is reduced between the isothermal process stages with a defined temperature profile of from 1 to 7 K per day (that is to say 24 h), preferably from 2 to 6 K per day, most preferably from 2 to 5 K per day. As a result of a stepwise or gradual reduction in the temperature, the temperature-dependent solubility product of the DTPMP, which has a tendency to supersaturation, in the aqueous crude product is reduced, the tendency to crystallisation of the dissolved DTPMP to DTPMP in the form of a crystalline solid being increased. Reducing the temperature advantageously has the effect of shortening the time required for the accumulation of larger amounts of crystalline solid containing DTPMP.

According to a particularly preferred embodiment of the process according to the invention, the defined temperature profile of the one-step process is divided into at least two stages, wherein the process temperature:
  a) for introduction of the seed crystals is first adjusted to a temperature in the range of from 25 to 85° C., more preferably from 30 to 80° C., most preferably from 35 to 75° C.,
  b) is then reduced stepwise or in a graduated manner by from 1 to 7 K per day, preferably from 2 to 6 K per day, most preferably from 2 to 5 K per day, and
  c) is subsequently kept constant (isothermal) for a defined period of time.

The process according to the invention for the quasi-continuous obtainment of a solid is preferably completed in steady-state operation under constant process conditions (constant temperature). Within the meaning of the invention, quasi-continuous means that the process for obtaining solid crystalline DTPMP is such that, after partial separation of accumulated crystallisate from the aqueous crude product, the process is continued and/or performed at least once more. During that time, a portion of aqueous crude product in the range of from 10 to 50% by mass is removed at specific time intervals, in particular every 0.5 to 12 hours, the amount removed being replaced by the addition of an identical amount of fresh aqueous crude product (as defined above). It can thereby be provided that seed crystals are purposively added to the amount of fresh aqueous crude product. In any case, the suspension density of the aqueous crude product is in the range of from 20 to 55% during the quasi-continuous obtainment of a solid.

The matured crystallisate is separated as described above from the amount of aqueous crude product removed.

The removal of at least a portion of aqueous crude product and the addition of an identical amount of fresh aqueous crude product preferably take place within the isothermal process stage.

The process according to the invention for the quasi-continuous obtainment of a solid is preferably carried out as a batch process in a stirred vessel.

The skilled person knows that a start-up phase is arranged between seeding and the steady-state operating phase. By definition, the start-up phase covers the period of time from seeding until the steady-state state is reached.

Within the meaning of the present invention, the period of time of the start-up phase (that is to say the period until transition to the steady-state operating state) is from 1 to 48 hours.

According to a preferred embodiment of the process according to the invention, the crystallisate is dried after it has been separated off so that, after drying, the separated crystallisate contains water in an amount by mass of not more than 25% by mass, preferably not more than 15% by mass, wherein water and optionally other volatile compounds (for example alcohols or ether) are preferably removed.

Drying preferably takes place at a temperature above 40° C., more preferably at temperatures above 50° C. Optionally or in addition, the separated crystallisate is dried by applying a vacuum.

If the content of dry matter in the separated crystallisate containing DTPMP is less than 60% by mass, the solid begins to dissolve in the residual moisture that is present at a temperature above about 40-50° C., which makes it necessary in industrial processes to provide an additional upstream pre-drying operation, which is expensive in terms of energy and apparatus. Preferably, therefore, after separation from the aqueous solution, only crystallisates that have a content of dry matter of more than 65% by mass are used for the drying.

The specific surface area of the separated crystallisate containing DTPMP in the form of a solid is preferably kept high by comminuting larger aggregates during the drying process. It can thereby optionally be provided that the dried crystallisate is comminuted coarsely or finely after the drying process for the purpose of better packaging and storage. A crystallisate having a homogeneous grain size distribution is advantageously obtained thereby. The grain size range can be adjusted by sieving, for example by means of a vibrating screen. By the parallel use of two mesh screens, individual grain fractions can purposively be obtained.

The methods of comminuting and/or pulverising crystallisates are known to the skilled person and include, for example, coarse grain crushers, pin mills and roller mills.

In addition, it has now been recognised that, during the drying of separated crystallisates containing DTPMP in the form of the pure acid by means of spray drying in the temperature range from 125 to 140° C., incongruent melting of the solid takes place, with the elimination of water. Known methods of drying solids containing DTPMP thus permit only the drying of sodium-containing DTPMP solids, wherein the DTPMP obtained after the synthesis is neutralised by the addition of sodium hydroxide solution, having a stoichiometric Na/DTPMP ratio of at least 2 to 1. The solid mixtures obtained thereby disadvantageously always contain DTPMP in the form of the $Na_xDTPMP$ salt (wherein x is a number in the range of from 2 to 10), so that it is not possible to isolate a solid that comprises DTPMP only in the form of the acid.

Surprisingly, however, it has now been found that, when drying is carried out below 125° C. until a stoichiometric Na/DTPMP ratio of 2 to 1 is present, a solid containing DTPMP in the form of the acid is obtained.

According to an alternative embodiment of the process according to the invention, therefore, drying is carried out by means of spray drying at a temperature below 125° C., more preferably below 120° C., most preferably in the temperature range of from 90 to 120° C.

Surprisingly, it has further been found that the crystallisation of the DTPMP and the formation of the crystallisate are advantageously accelerated in an aqueous crude product comprising up to 5% by mass of a strong acid. Strong acids are preferably selected from the group of the mineral acids and/or organic acids, which are present in the aqueous crude product either as a result of the synthesis or through purposive addition.

According to an embodiment according to the invention, the aqueous crude product contains strong acids, preferably mineral acid, such as, for example, a hydrohalic acid, carboxylic acid, phosphoric acid or sulfuric acid, in particular a hydrohalic acid, most preferably hydrochloric acid, in a total amount in the range of from 1 to 5% by mass, preferably in the range of from 1 to 4.5% by mass. However, aqueous crude products having a total content of mineral acids in the range of from 1 to 4% by mass are also used.

The addition of a highly concentrated acid preferably effects the defined adjustment of the pH, so that DTPMP is present in the aqueous crude product advantageously in the form of the electrically neutral derivative and/or in the form of the positively charged derivative. The five phosphonic acid groups ($—PO_3^{2-}$) of DTPMP are preferably completely or at least partially in their protonated form, the amino groups advantageously being present in protonated form as the quaternary amine.

The crystallisate obtained by the process according to the invention is optionally obtained by recrystallisation one or more times and optionally with intermediate synthesis processes in order to minimise secondary synthesis products.

Methods of recrystallisation are very well known to the skilled person, the solution from which the DTPMP obtained by a process according to the invention is recrystallised preferably being contacted with a sufficient amount of seed crystals, and kinetic energy being inputted at the same time.

The aminoalkylenephosphonic acid DTPMP is known per se. However, at the present time, a solid of the pure acid DTPMP has not been described, nor is there any information about crystal modifications thereof.

When solids are used industrially as chemical raw materials, they are generally in the form of loose bulk goods. Quality parameters, such as easy metering and storage stability, of these solids are essential requirements for the successful use thereof.

However, the high adhesive tendency which occurs during the process of drying commercial DTPMP grades (for example sodium salts) limits the use of thermal drying methods considerably. Modern fluidised bed processes can thus be carried out only with a low drying performance and with the addition of carriers (accompanying substances). These carriers are to reduce the adhesion of individual product grains during production and lower the hygroscopicity during storage, but at the same time they introduce into the product accompanying substances (for example silicates) which are of a different type to the active substance DTPMP and are generally undesirable, and additionally reduce the active content of the product considerably. Because of their extremely high hygroscopicity, spray-dried powders cake in a very short time and can thus no longer be metered. For these reasons, DTPMP solids produced by means of thermal drying processes have to date not been able to establish themselves on an industrial scale.

Particularly disadvantageously, known solids of the salts of DTPMP (for example sodium salts) contain, owing to their production, high fractions of additives (accompanying substances) with, at the same time, low fractions (less than 40% by mass) of DTPMP in those solids. Nevertheless, the solids of the salts of DTPMP are disadvantageously highly hygroscopic, so that dried solids clump together to form a pasty mass (adhesive tendency) even in a closed container. Portioning is consequently more difficult for the formulator, which in turn limits the scope of application of known dried substances.

Accordingly, it is likewise an object of the invention to provide a solid of the pure acid DTPMP.

Chemical compounds can exist in different crystal modifications and thereby tend to form a wide variety of particulate structures, such as, for example, needles or plates, which differ in terms of their macroscopic properties. Needles, for example, have a significantly lower bulk density compared with plates, which is a disadvantage for the storage or transport of the compound. Another important aspect for an industrial application is whether a chemical compound is in the form of a crystallisate or an amorphous material, the latter having the disadvantageous tendency to form large, irregular agglomerates. Essential factors for economical and technical usability are crystallite size (that is to say, the larger the crystallisate, the more favourable it is, since the proportion of the surface area in the volume is low) and crystal form (that is to say, compact crystallisates are better to handle than forms which tend to generate texture, for example needles or plates), since they have a direct influence on the specific surface area and on filterability, washability, dryability and hygroscopicity.

Surprisingly, three crystal modifications of the pure acid DTPMP have now been found, the pure acid DTPMP, preferably in the form of the pure hydrate, having the general formula (I):

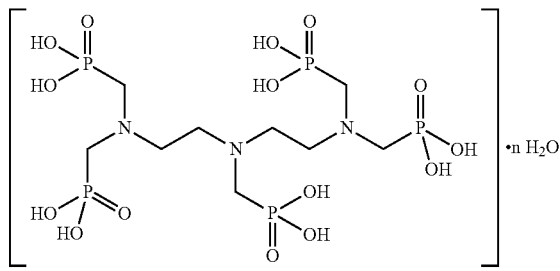
(I)

wherein n is a number between 0 and 2, preferably between 0.5 and 1.5.

The three crystal modifications of pure DTPMP are distinguished by the characteristic chemical shifts in a $^1$H-NMR spectrum or $^{31}$P-NMR spectrum (measured at pH 6.5) shown in FIG. 1 and listed below:

$^1$H NMR (500 MHz, D$_2$O; ppm): Δ=3.52 (t, J=6.3 Hz, 4H), 3.19 (d, J=11.6 Hz, 8H), 3.01 (t, J=6.2 Hz, 4H), 2.66 (d, J=11.2 Hz, 2H).

$^{31}$P NMR (202 MHz, D$_2$O; ppm): Δ=16.58 (t, J=11.1 Hz), 7.40 (t, J=11.5 Hz).

It has been shown particularly advantageously that the crystallisates according to the invention containing DTPMP as the pure acid are not hygroscopic and therefore, unlike the salts of DTPMP, do not clump together to form a pasty mass. Consequently, the DTPMP is easier to portion, which opens up a large number of new possible uses to the formulator.

By definition, the term "hygroscopicity" denotes the ability of solids to absorb moisture from the surroundings, that is to say to react to the relative moisture content of the air at a specific temperature by absorbing or eliminating water vapour. Most moisture-absorbing solids undesirably dissolve or form clumps as a result of water absorption.

The crystallisate of the pure acid DTPMP according to the invention, in particular the crystal modifications α, β and γ, preferably has a hygroscopicity of less than 1% by mass of water per 10 days at a temperature of 22° C. and a relative humidity of 55% by mass. More preferably, the hygroscopicity of the crystallisate according to the invention under the above-mentioned conditions is less than 1% by mass of water per 20 days.

Against this background, it is an additional object of the present invention to provide a first crystal modification of the pure acid DTPMP under the name according to the invention α crystal modification, wherein the corresponding X-ray diffraction diagram of the α crystal modification (obtained by Cu-K$_α$ radiation [1.54178 Å] at 25° C.) is distinguished by characteristic reflections at the following double diffraction angles 2Θ (in degrees) and lattice plane spacings d in Å$^{-1}$, wherein all the reflection positions are affected by an uncertainty of ±0.2°:

| α crystal modification | | |
|---|---|---|
| 2Θ | d | Rel. intensity |
| 6.8 | 13.00 | 38.00% |
| 17.9 | 5.0 | 35.60% |
| 20.2 | 4.40 | 41.00% |
| 22.2 | 4.00 | 45.80% |
| 22.5 | 3.95 | 100.00% |
| 23.0 | 3.86 | 72.60% |
| 23.1 | 3.84 | 39.10% |
| 25.0 | 3.6 | 64.30% |

An X-ray diffraction diagram, recorded with Cu-K$_α$1 radiation, of crystallisates of the α crystal modification according to the invention is shown in FIG. 2 and proves the absence of another crystal modification. Absence of another crystal modification means that both the β and the γ crystal modification of the pure acid DTPMP are no longer detectable by known analytical methods.

The α crystal modification preferably comprises DTPMP in the form of the crystalline monohydrate of the pure acid DTPMP (that is to say in which all the phosphonic acid groups are protonated). The crystallisates of the α crystal modification according to the invention can contain water molecules in the crystal lattice, normally up to 4% by mass, based on the total weight.

Surprisingly, it has been found that (unlike crystallisates of the β crystal modification) only crystallisates of the α crystal modification grow epitaxially on crystallisates of the γ crystal modification. The epitaxial growth can advantageously be utilised for the purposive crystallisation of compact crystallisates at moderate temperatures by using the crystallisates of the γ crystal modification as seed material, but the crystallisation process takes place in the existence range of the α crystal modification. This epitaxy is also a clear and unambiguous distinguishing feature for delimiting the α and β crystal modifications from one another.

The α crystal modification is preferably obtained by a process according to the invention. A pure or predominantly pure α crystal modification is more preferably formed when an aqueous solution having a pH of less than 2 is used as starting material. The aqueous crude product preferably contains DTPMP with a total fraction in the range of from 10 to 35% by mass, more preferably from 10 to 30% by mass.

The aqueous crude product for the production of the α crystal modification preferably has a temperature in the range of from 0 to 40° C., more preferably from 5 to 35° C.

Surprisingly, it has been found that it is sufficient for the production of crystallisates of the α crystal modification, which have an edge length of only a maximum of 20 μm, to use as the seed crystal a seed material with a total fraction of DTPMP in the range of from 30 to 95% by mass.

Crystallisates of the α crystal modification are preferably plate-like and have an aspect ratio (length to width) in the range of from 1:1 to 10:1 and a width-to-depth ratio of at least 5:1. The volume-based specific surface area of crystallisates of the α crystal modification is preferably above 1.0 m$^2$/m$^3$.

The volume-based specific surface area of a body is defined as the ratio of its surface area (in m$^2$) to its volume (in m$^3$).

Hygroscopicity refers to the affinity of a substance to absorb water. It is known to the skilled person that hygroscopicity is substance-specific and is dependent both on purity (that is to say, the purer the substance, the lower its hygroscopicity) and on the volume-based surface area (the smaller the specific surface area, the lower the hygroscopicity).

According to a preferred embodiment of the present invention, crystallisates of the α crystal modification can be obtained, for example, by a process in which, immediately after the synthesis of the DTPMP, a multi-step purification process takes place, so that a pre-purification by precipitation at about 30° C. is first carried out. The resulting precipitate is separated from the reaction solution and again converted into a solution in a downstream reactor in concentrated form. After being crystallised again, the solid obtained is isolated and subjected to drying. The solid obtained consists of plate-like crystallisates which have an edge length of approximately 20 µm and some of which have grown together to form aggregates.

Surprisingly, it has additionally been found that a second, hitherto unknown crystal modification of the pure acid DTPMP is formed by a process according to the invention at a slightly elevated pH. The second crystal modification is referred to as the β crystal modification.

Accordingly, the present invention provides a β crystal modification of the pure acid DTPMP, wherein the corresponding X-ray diffraction diagram of the β crystal modification (obtained by Cu-K$_\alpha$ radiation) is distinguished by characteristic reflections at the following double diffraction angles 2Θ (in degrees) and lattice plane spacings d in Å$^{-1}$, wherein all the reflection positions are affected by an uncertainty of ±0.2°:

| β crystal modification | | |
| --- | --- | --- |
| 2Θ | D | Rel. intensity |
| 6.7 | 13.17 | 41.30% |
| 18.6 | 4.77 | 43.80% |
| 19.6 | 4.5 | 36.50% |
| 20.0 | 4.4 | 39.80% |
| 22.1 | 4.0 | 65.10% |
| 22.5 | 3.9 | 79.10% |
| 23.0 | 3.9 | 76.80% |
| 24.8 | 3.6 | 50.60% |
| 25.2 | 3.5 | 35.70% |

An X-ray diffraction diagram, recorded with Cu-K$_\alpha$1 radiation, of crystallisates of the β crystal modification according to the invention is shown in FIG. 4 and proves the absence of another crystal modification. Absence of another crystal modification means that neither the α nor the γ crystal modification of the pure acid DTPMP is detectable by known analytical methods.

The β crystal modification preferably comprises DTPMP in the form of the crystalline monohydrate of the pure acid DTPMP (that is to say in which all the phosphonic acid groups are protonated). The crystallisates of the β crystal modification according to the invention can contain water molecules in the crystal lattice, normally up to 4% by mass, based on the total weight.

The β crystal modification is preferably obtained by a process according to the invention. A pure or predominantly pure β crystal modification is more preferably formed when an aqueous solution having a pH of less than 4, preferably less than 3, is used as starting material. The pH is preferably adjusted by addition of a highly concentrated lye, preferably an alkaline lye such as, for example, sodium hydroxide solution. The aqueous crude product preferably contains DTPMP with a total fraction in the range of from 15 to 55% by mass, more preferably from 15 to 50% by mass. A range from 20 to 45% by mass is most preferred.

The aqueous crude product for the production of the β crystal modification preferably has a temperature in the range of from 5 to 60° C., more preferably from 35 to 55° C.

Crystallisates of the β crystal modification are preferably lance-shaped (that is to say cutter-shaped) and have an aspect ratio (length to width) of at least 3:1, more preferably at least 10:1, and a width-to-depth ratio of at least 5:1. The volume-based specific surface area of crystallisates of the β crystal modification is preferably in the range of from 0.2 to 1.2 m$^2$/m$^3$, so that only a small amount of retained water remains on the surface of separated crystallisates. In the case of crystallisates of the β crystal modification it is thus advantageously possible to dispense wholly or at least partially with subsequent drying (as described above).

The present invention also provides a third, hitherto unknown triclinic crystal modification of the pure acid DTPMP. The third crystal modification is referred to as the γ crystal modification.

The X-ray diffraction diagram of the triclinic γ crystal modification (obtained by Cu-K$_\alpha$ radiation) is distinguished by characteristic reflections at the following double diffraction angles 2Θ (in degrees) and lattice plane spacings d in Å$^{-1}$, wherein all the reflection positions are affected by an uncertainty of ±0.2°:

| γ crystal modification | | |
| --- | --- | --- |
| 2Θ | d | Rel. Intensity |
| 13.0 | 6.8 | 48.10% |
| 17.9 | 4.9 | 37.20% |
| 22.0 | 4.0 | 39.20% |
| 22.4 | 4.0 | 100.00% |
| 23.1 | 3.8 | 64.40% |
| 23.3 | 3.8 | 44.90% |
| 25.1 | 3.6 | 92.60% |
| 26.1 | 3.4 | 36.00% |

An X-ray diffraction diagram, recorded with Cu-K$_\alpha$1 radiation, of crystallisates of the γ crystal modification according to the invention is shown in FIG. 6 and proves the absence of another crystal modification. Absence of another crystal modification means that neither the α nor the β crystal modification of the pure acid DTPMP is detectable by known analytical methods.

The γ crystal modification preferably comprises DTPMP in the form of the crystalline monohydrate of the pure acid DTPMP (that is to say in which all the phosphonic acid groups are protonated). The crystallisates of the γ crystal modification according to the invention can contain water molecules in the crystal lattice, normally up to 4% by mass, based on the total weight.

The γ crystal modification is preferably obtained by a process according to the invention. A pure or predominantly pure γ crystal modification is more preferably formed when an aqueous solution having a pH of less than 4, preferably less than 3, is used as starting material. The pH is preferably adjusted by addition of a highly concentrated lye, preferably an alkaline lye such as, for example, sodium hydroxide solution. The aqueous crude product preferably contains DTPMP with a total fraction of at least 45% by mass, more preferably in the range of from 45 to 60% by mass, most preferably from 45 to 55% by mass.

The γ crystal modification is preferably obtained when an aqueous solution is heated to a temperature in the range of from 40 to 85° C., more preferably from 50 to 80° C., most preferably to over 55° C.

Crystallisates of the γ modification are preferably cuboid to column-shaped and have an aspect ratio (length to width) in the range of from 1:1 to 10:1 and a width-to-depth ratio of not more than 5:1. The volume-based specific surface area of crystallisates of the γ crystal modification is preferably less than 0.3 m$^2$/m$^3$, so that only a small amount of retained water to no retained water remains on the surface of separated crystallisates. In the case of crystallisates of the γ crystal modification it is thus advantageously possible to dispense wholly with subsequent drying (as described above). Most preferably, crystals of the γ crystal modification can be processed simply by pelletising. Particularly advantageously, high degrees of purity can be achieved for crystallisates of the γ crystal modification, which have only a small volume-based specific surface area, even without a washing step following the separation.

The present invention also provides an aqueous solution which contains crystallisates of the pure acid DTPMP according to the general formula (I), preferably in the α crystal modification and/or β crystal modification and/or γ crystal modification.

An aqueous solution within the meaning of the invention is preferably obtainable by a process according to the invention.

An aqueous solution containing crystallisates in one of the crystal modifications according to the invention can optionally also be obtained by suspending crystallisates of at least one crystal modification according to the invention in water or a water-containing solution. This is the case, for example, when crystallisates, after being separated off, are washed or dissolved for a potential use of the DTPMP in water or a water-containing solution.

It can also be provided that the crystallisates of the pure acid DTPMP in the α crystal modification and/or β crystal modification and/or γ crystal modification are introduced into water or a water-containing solution for long-term storage and/or for transport.

The invention also provides the use of a process according to the invention for purifying an aqueous crude product containing DTPMP in pure form with a total content of at least 5% by mass, preferably from 10 to 85% by mass, more preferably from 20 to 80% by mass.

A particularly advantageous use of the process according to the invention consists in applying it directly after a preparation process for the synthesis of DTPMP. The aqueous solution containing DTPMP that is to be purified is thereby fed to the process according to the invention directly or via temporary storage after the last reaction step. According to a particularly advantageous embodiment of the process according to the invention, the quasi-continuous obtainment of solid takes place in a stirrer vessel.

A process according to the invention is preferably used to produce, preferably on an industrial scale, a crystallisate of the pure acid DTPMP according to the general formula (I), preferably in the α crystal modification and/or β crystal modification and/or γ crystal modification, with a total content of DTPMP in pure form of at least 75% by mass, preferably at least 80% by mass.

A crystallisate obtained by the process according to the invention for obtaining solid can be used directly as a solid or by being dissolved or suspended in water or an aqueous solution. The form in which the crystallisate is used depends on the wishes and needs of the formulator at the particular usage site. It can be provided that the crystallisate obtained is processed by spray drying, agglomeration or pelletising.

BRIEF DESCRIPTION OF THE DRAWINGS

The invention is to be described in greater detail by means of the following figures and embodiments, without limiting the invention thereto.

EXAMPLES

Example 1—Isothermal Procedure

Figure 1:
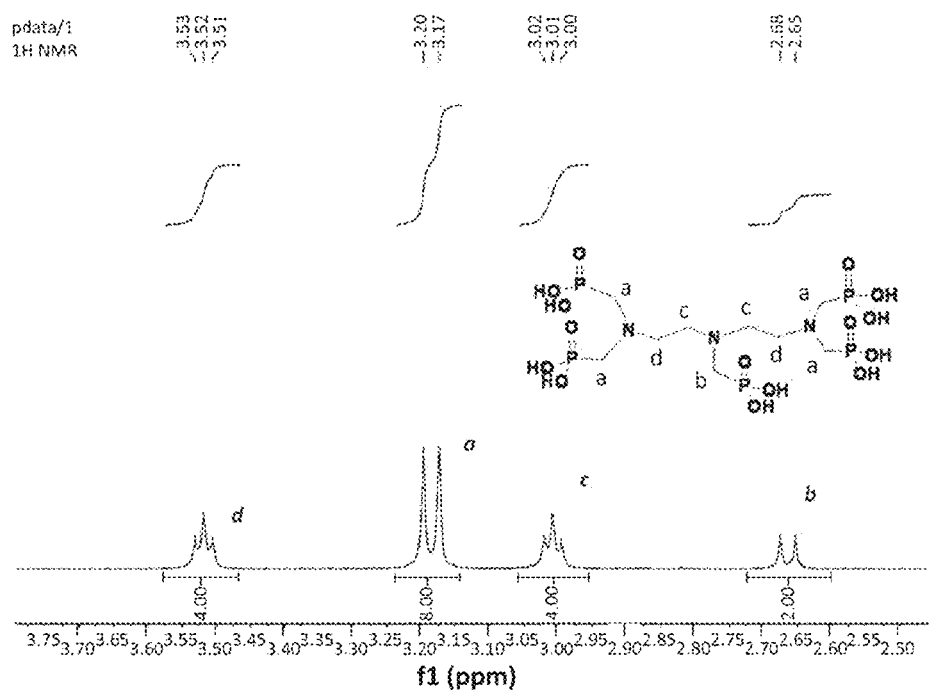
FIG. 1: top: $^1$H-NMR of DTPMP crystallisates; bottom: $^{31}$P-NMR of DTPMP crystallisates.
Figure 1:
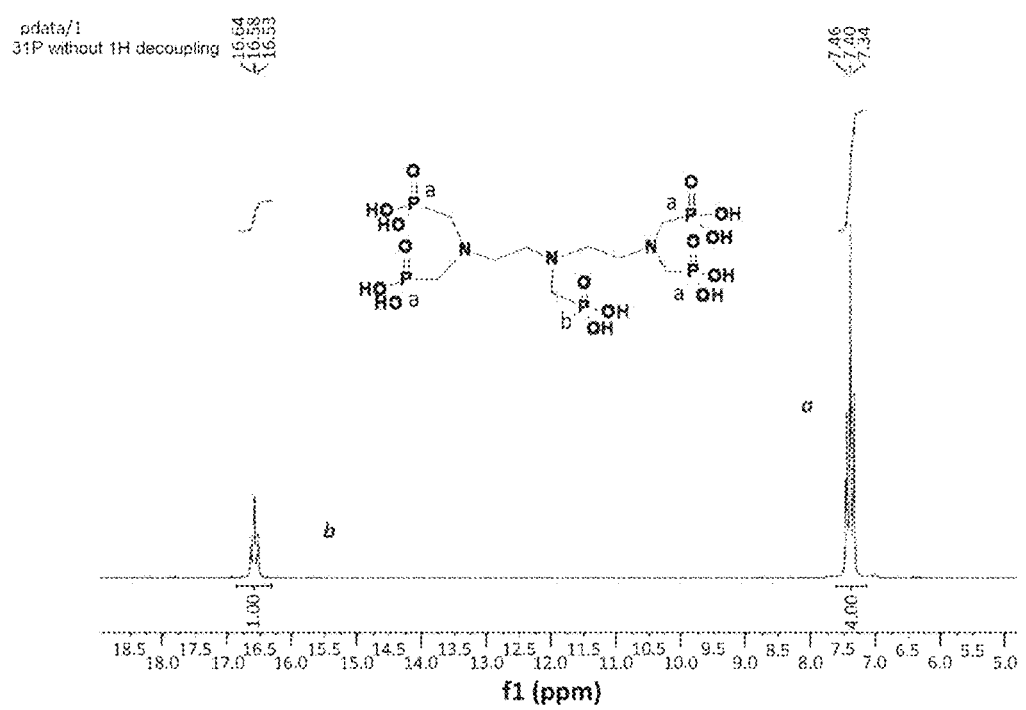

A starting amount of 4.5 kg of slurry, containing 40% by mass DTPMP and 3% by mass chloride in water, is placed in a double-walled 5-litre stirred tank reactor having a 14 cm anchor agitator. Seeding was carried out with 0.2 kg of solid containing 85% by mass DTPMP and 0.1% by mass chloride and having a main particle size of 20 μm. A calculated initial suspension density of 4% by mass was obtained. Precipitation took place at a constant stirring speed of 150 rpm.

A temperature profile is specified during the quasi-continuous process, whereby the temperature of the aqueous solution is first increased continuously over a period of 18 hours to a temperature of 58° C. and then the temperature is cooled continuously over a period of 72 hours by 1 K per 8 hours to a temperature of 46° C. and then kept constant for 70 hours. Samples of the slurry were removed at various times, and both the solution and the suspended solid were tested for their contents of DTPMP and chloride.

| Test time | Temperature [° C.] | Suspension density [% by mass] | DTPMP solution [% by mass] | Chloride solution [% by mass] | DTPMP solid [% by mass] | Chloride solid [% by mass] |
|---|---|---|---|---|---|---|
| 0.5 | 58 | 14 | 38.9 | 3.0 | 55.2 | 2.1 |
| 18 | 58 | 16 | 39.6 | 3.1 | 53.1 | 2.2 |
| 24 | 58 | 16 | 38.9 | 3.1 | 54.3 | 2.2 |
| 42 | 55 | 21 | 39.2 | 3.1 | 53.2 | 2.2 |
| 48 | 54 | 21 | 39.8 | 3.2 | 52 | 2.3 |
| 66 | 51 | 30 | 36.3 | 3.2 | 50.8 | 2.4 |
| 72 | 50 | 33 | 37.5 | 3.2 | 52.6 | 2.4 |
| 90 | 46 | 44 | 34.3 | 3.4 | 49.5 | 2.4 |
| 96 | 46 | 48 | 33.9 | 3.4 | 48.8 | 2.5 |
| 115 | 46 | 59 | 31.8 | 3.6 | 47.4 | 2.5 |
| 140 | 46 | 67 | 29.6 | 3.7 | 49 | 2.6 |
| 161 | 46 | 73 | 29 | 3.9 | 45.8 | 2.6 |

Separation of the crystallisate from the aqueous solution takes place in a filtering centrifuge having a perforated drum with a filtering area of 235 cm² and at a centrifugation speed of 6500 rpm for 2 minutes. This centrifugation speed of 6500 rpm corresponds to a separating capacity of 3500 g. Three washing operations with washing water (corresponding to half the amount of solid, divided into 3 equal amounts) are then carried out. Finally, the separated crystallisate is dried for 5 minutes at a centrifugation speed of 10,000 rpm. This centrifugation speed of 10,000 rpm corresponds to a separating capacity of 8400 g.

The particle sizes of the DTPMP crystallisates are determined by means of a laser diffraction particle size analyser LS 13 320/Beckmann Coulter at a wavelength of 780 nm.

| | |
|---|---|
| Mean [µm] | 60 |
| $d_{10}$ [µm] | 17 |
| $d_{90}$ [µm] | 113 |

For characterising the breadth of a particle size distribution, the $d_{10}$ and the $d_{90}$ value are used in addition to the $d_{50}$ value. The $d_{50}$ value (mean) indicates the mean particle diameter, that is to say that exactly 50% of the particles are larger than or smaller than the indicated particle diameter, and is called the main particle size in the following. The $d_{10}$ value refers to the particle diameter at which 10% of the particles are smaller than this limit value.

Correspondingly, the $d_{90}$ value indicates a particle diameter at which 90% of the particles are smaller than the indicated limit value.

Figure 5:
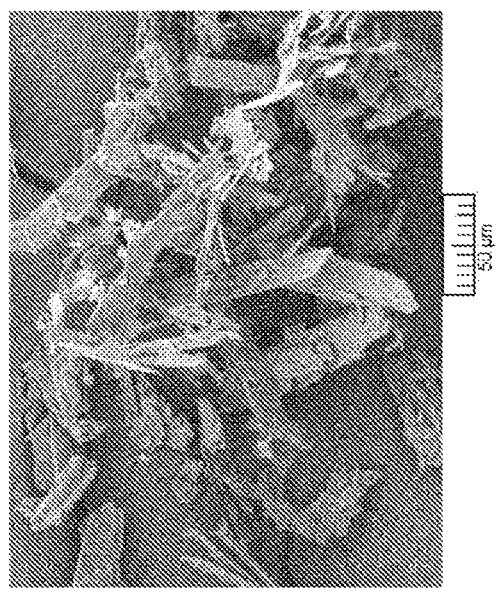
FIG. 5: top: light micrograph of plate-like crystallisates of the β crystal modification; bottom: SEM micrographs thereof.
Figure 5:
Figure 5:
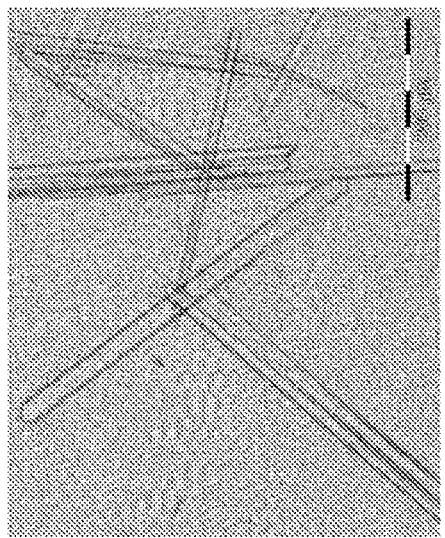

The crystallisates of the isolated solid have a cutter shape with an edge length of from 50 to 120 µm, a width of from 10 to 50 µm and a thickness in the range of from 1 to 5 µm (cf. FIG. 5, top left image).

Following the test, the contents of DTPMP and chloride in the individual components were determined by complexometric titration and by argentometric titration, respectively.

| | Amount obtained, based on the amount of slurry | DTPMP content [% by mass] | Chloride content [% by mass] |
|---|---|---|---|
| Slurry | 4.5 [kg] | 40 | 3 |
| Solid unwashed | 34 [% by mass] | 83.6 | 0.6 |
| Solid washed | 23 [% by mass] | 87.2 | 0.1 |
| Filtrate | 65 [% by mass] | 26.9 | 3.8 |
| Washing water | 29 [% by mass] | 12.1 | 1.5 |

Example 2—Continuous Procedure

For continuous long-term production in the state over a total period of 8 weeks on an industrial scale, a starting amount of 10 kg of slurry, containing 40% by mass DTPMP and 3% by mass chloride in water, is placed in a 10-litre stirred tank reactor having an 11 cm propeller mixer. Seeding is carried out once by the introduction of 2 kg of solid containing 85% by mass DTPMP and 0.1% by mass chloride and characterised by a main particle size of 35 µm. A calculated initial suspension density of 14% by mass is obtained. Precipitation takes place at a constant temperature of 40° C. and at a constant stirring speed of 280 rpm.

During quasi-continuous long-term production, 2.5 kg of suspension are removed every 12 hours, the amount removed being replaced by the addition of an identical amount of fresh suspension (40% by mass DTPMP and 3% by mass chloride). Depending on the time at which the samples are removed, the suspension density, determined gravimetrically by means of centrifugation at 6500 rpm/2 minutes, is from 30 to 45%. This centrifugation speed of 6500 rpm corresponds to a separating capacity of 3500 g.

The crystallisate is separated from the amount of slurry removed in a filtering centrifuge having a perforated drum with a filtering area of 235 cm² and at a centrifugation speed of 6500 rpm for 2 minutes. This centrifugation speed of 6500 rpm corresponds to a separating capacity of 3500 g. Three washing operations with washing water (corresponding to half the amount of solid, divided into 3 equal amounts) are then carried out. Finally, the separated crystallisate is dried for 5 minutes at a centrifugation speed of 10,000 rpm. This centrifugation speed of 10,000 rpm corresponds to a separating capacity of 8400 g.

The particle sizes of the DTPMP crystallisates are determined by means of a laser diffraction particle size analyser LS 13 320/Beckmann Coulter at a wavelength of 780 nm. The crystallisates of the isolated solid have a lance shape with an edge length of from 50 to 100 µm, a width of from 10 to 50 µm and a thickness in the range of from 1 to 5 µm (cf. FIG. 5; SEM micrograph).

| | |
|---|---|
| $d_{50}$ [µm] | 50 |
| $d_{10}$ [µm] | 10 |
| $d_{90}$ [µm] | 95 |

Following the test, the contents of DTPMP and chloride in the individual components were determined analogously to Example 1.

Example 3—Influence of Seeding and Kinetic Energy Input

In order to determine the influences of seeding and kinetic energy input on the stirring speed and the space-time yield (amount of crystallisate formed per crystallisation volume and per unit time), the tests described below were carried out as follows.

A 250 ml screw-top jar clamped in a stand and provided with a perforated lid in order to reduce evaporative losses was equipped with a propeller mixer having a 4 cm stirring member driven by a stirring mechanism. The test setup was operated at room temperature in a fume cupboard.

An aqueous solution comprising 25% by mass DTPMP was used as the slurry. The solid DTPMP acid used to prepare the slurry had, upon initial weighing, a content of 49.6% by mass DTPMP acid, 1.7% by mass chloride and 0.2% by mass orthophosphate as well as a main particle size of 15 μm. This material was also used as the seed material. For seeding the slurry, the amount of solid DTPMP acid specified for the test was made into a suspension in a few millilitres of the slurry and introduced into the precipitation vessel by means of a pipette. The amount used was calculated as g of seed material per 100 g of slurry.

The progress of crystallisation is determined by repeated measurements (according to the following table) of the DTPMP content in the filtrate.

In order to determine the DTPMP content remaining in the slurry, samples were removed via a 45 μm syringe filter and analysed by means of complexometric titration.

Result

As shown in the following table, the combination of high stirring speed PLUS a large amount of seed material in test 1-1 results in the quickest depletion of the mother liquor and thus produces the greatest yield of crystallisate per unit time.

Tests 2-1 and 3-1 here demonstrate that stirring, that is to say the input of kinetic energy, is the dominant factor. At a constantly high stirring speed, tests 1-1, 2-1 and 3-1 show a clear advantage for the larger amounts of seed material.

| | Test no. | | | | | |
|---|---|---|---|---|---|---|
| | 1-1 | 2-1 | 2-3 | 3-1 | 3-2 | 3-3 |
| Seed amount [% by mass] | 5 | 0.5 | 0.5 | 0.1 | 0.1 | 0.1 |
| Resulting initial suspension density [% by mass] | 2.4 | 0.25 | 0.25 | 0.05 | 0.05 | 0.05 |
| Stirring [rpm] | 160 | 160 | 0 | 160 | 40 | 0 |
| Run time [h] | DTPMP in the filtrate [% by mass] | DTPMP in the filtrate [% by mass] | DTPMP in the filtrate [% by mass] | DTPMP in the filtrate [% by mass] | DTPMP in the filtrate [% by mass] | DTPMP in the filtrate [% by mass] |
| 0 | 25.0 | 25.0 | 25.0 | 25.0 | 25.0 | 25.0 |
| 2 | | | 25.0 | | | |
| 4 | | | | | 23.6 | 23.6 |
| 15 | 7.5 | | | 18.4 | | |
| 16 | | 10.5 | | | | |
| 21 | | | 14.6 | | 17.1 | 19.8 |
| 23 | 7.5 | 8.8 | | 14.4 | | |
| 24 | | | | | 15.4 | 19.7 |
| 26 | | | 13.7 | | | |
| 28 | | | | | 13.9 | 19.6 |
| 39 | 7.1 | | | | | |
| 40 | | 7.4 | | 8.6 | | |
| 46 | | | | 8.6 | | |
| 47 | 7.5 | 7.4 | | | | |
| 63 | 6.9 | | | | | |
| 64 | | 7.2 | | 7.4 | | |
| 69 | | | 10.8 | | 7.7 | 17.8 |
| 71 | 6.9 | 7.6 | | 7.1 | | |
| 94 | | | | | | 17.1 |
| 99 | | | | | | 16.8 |
| 140 | | | | | 6.7 | |
| 165 | | | | | | 15.0 |

Example 4—Process for the Production of the γ Crystal Modification, Isothermal at 70° C. and 60° C.

A starting amount of 2 kg of slurry, containing 55% by mass DTPMP, 3.9% by mass chloride and 0.7% by mass ortho-phosphate, is placed in a double-walled 3-litre stirred reactor having a 14 cm anchor agitator. Seeding was carried out once with 140 g (about 7% by mass) of crystallisate of the γ crystal modification comprising 82.5% by mass DTPMP and 0.09% by mass chloride and having a main particle size of 50 μm. Precipitation took place at a constant stirring speed of 180 rpm.

The quasi-continuous process is left isothermal over a period of 19 days. The crystallisation is first left at a constant initial temperature of 70° C. for 7 days and then the temperature is lowered to 60° C. and left for a remaining period of 12 days. The matured crystallisate is separated from the aqueous solution in a filtering centrifuge having a perforated drum with a filtering area of 235 cm$^2$ and at a centrifugation speed of 6800 rpm for 2 minutes. This centrifugation speed of 6500 rpm corresponds to a separating capacity of 3500 g. Three washing operations with washing water (corresponding to half the amount of solid, divided into 3 equal amounts) are then carried out. Finally, the separated crystallisate is dried for 5 minutes at a centrifugation speed of 10,000 rpm. This centrifugation speed of 10,000 rpm corresponds to a separating capacity of 8400 g.

The suspension density, that is to say the solids content of the suspension in % by mass, is determined gravimetrically via a benchtop centrifuge in 12 ml vials at 6500 rpm. This centrifugation speed of 6500 rpm corresponds to a separating capacity of 3500 g.

Analytical values during isothermal procedure at 70° C.:

| | DTPMP content [% by mass] | Chloride content [% by mass] | Chloride fraction in DTPMP [% by mass] | Amount [g] |
|---|---|---|---|---|
| Filtrate | 49.8 | 2.69 | 5.2 | 789 |
| Solid unwashed | 90.9 | 0.28 | 0.31 | 1290 |
| Solid washed | 93.8 | 0.06 | 0.06 | 941 |

Analytical values during isothermal procedure at 60° C.:

| | DTPMP content [% by mass] | Chloride content [% by mass] | Chloride fraction in DTPMP [% by mass] | Amount [g] |
|---|---|---|---|---|
| Filtrate | 48.7 | 2.94 | 6.03 | 511 |
| Solid unwashed | 89.8 | 0.4 | 0.45 | 1470 |
| Solid washed | 92.8 | 0.03 | 0.03 | 895 |

The particle size of the DTPMP crystallisates is then determined by means of a laser diffraction particle size analyser LS 13 320/Beckmann Coulter at a wavelength of 780 nm. The average growth rate (in [μm/h]) of the crystallisates was determined for an isothermal procedure at 70° C. as 0.15.

|  | Start | End |
|---|---|---|
| $d_{50}$ [μm] | 50 | 68 |
| $d_{10}$ [μm] | 22 | 39 |
| $d_{90}$ [μm] | 88 | 103 |

For characterising the breadth of a particle size distribution, the $d_{10}$ and the $d_{90}$ value are used in addition to the $d_{50}$ value. The $d_{50}$ so value (mean) indicates the mean particle diameter, that is to say that exactly 50% of the particles are larger than or smaller than the indicated particle diameter, and is called the main particle size in the following. The $d_{10}$ value refers to the particle diameter at which 10% of the particles are smaller than this limit value. Correspondingly, the $d_{90}$ value indicates a particle diameter at which 90% of the particles are smaller than the indicated limit value.

Because of the small specific surface area of crystallisates of the γ crystal modification, both tests, 60° C. and 70° C., for obtaining the γ crystal modification advantageously yield, even without washing, very pure solids which, as a result of the low residual moisture contents of <10% by mass, can be dried significantly more efficiently than is the case with the other crystal forms. When the filter cake of crystallisates of the γ crystal modification is washed analogously to examples 5 and 6, residual moisture and impurities can advantageously be reduced further.

Figure 6:
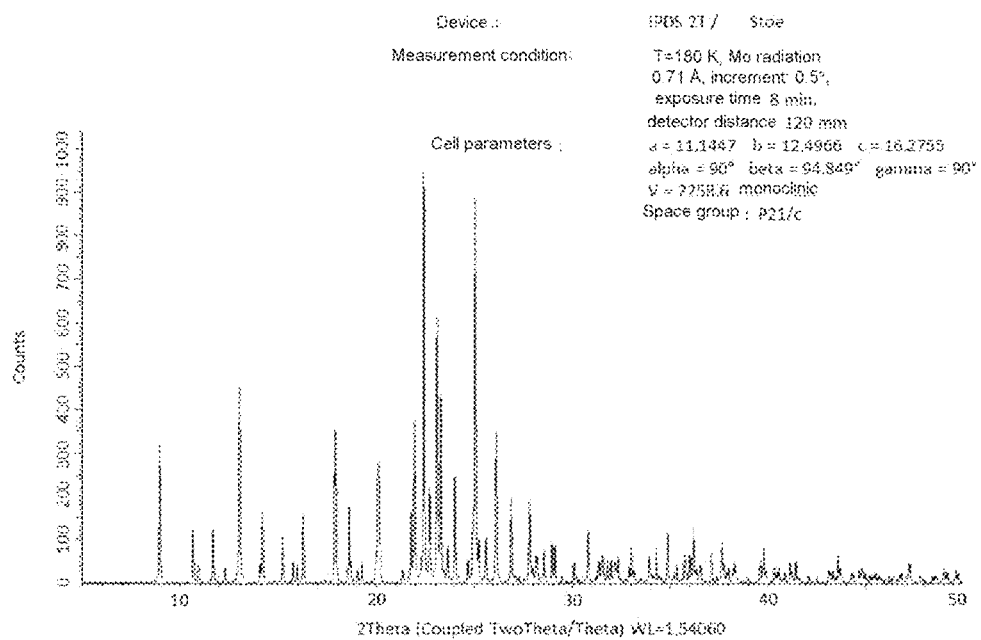
FIG. 6: calculated powder diffractogram of crystallisates of the γ crystal modification.
Figure 7:
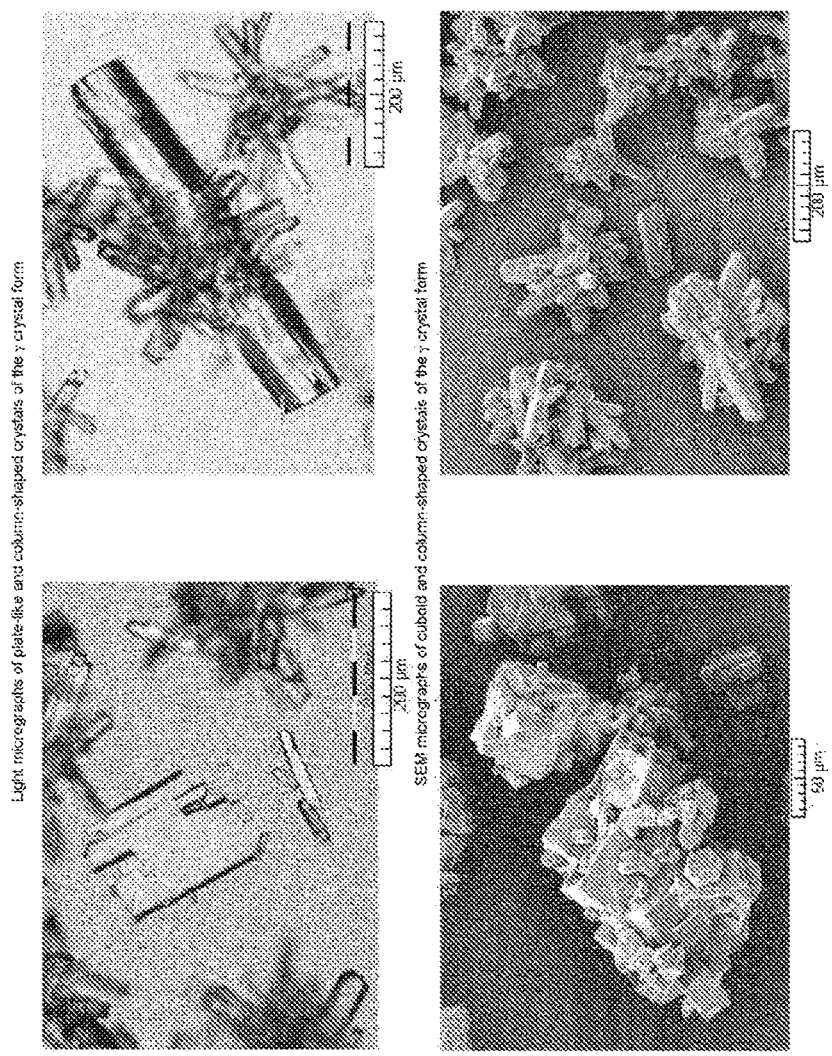
FIG. 7: top: light micrograph of plate-like crystallisates of the γ crystal modification; bottom: SEM micrographs thereof.
Figure 8:
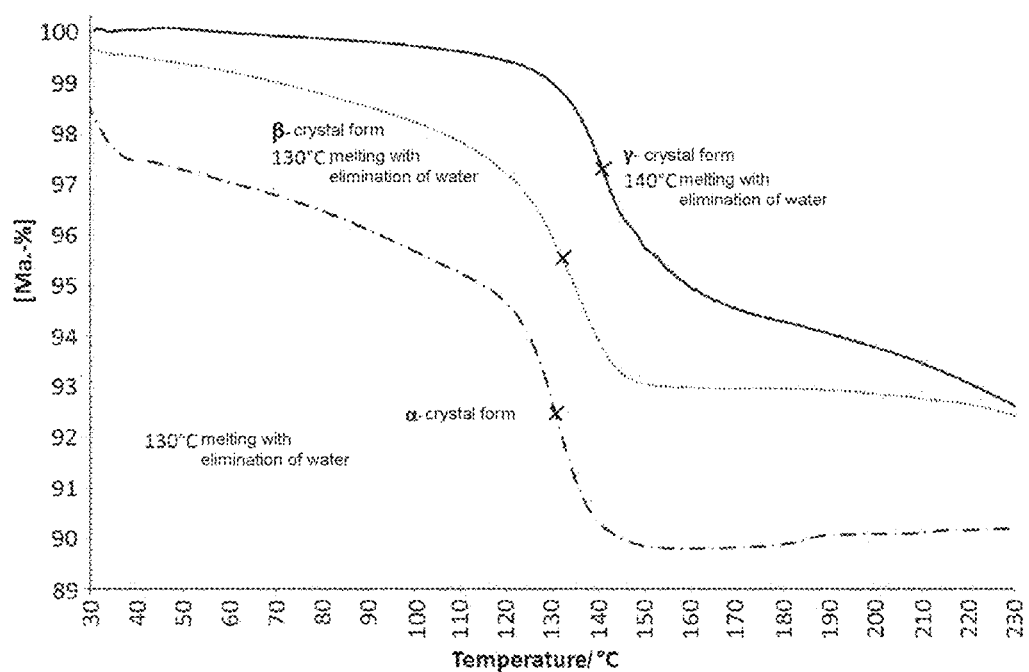
FIG. 8: thermogravimetry of crystallisates of the α, β and γ crystal modification.
Figure 10:
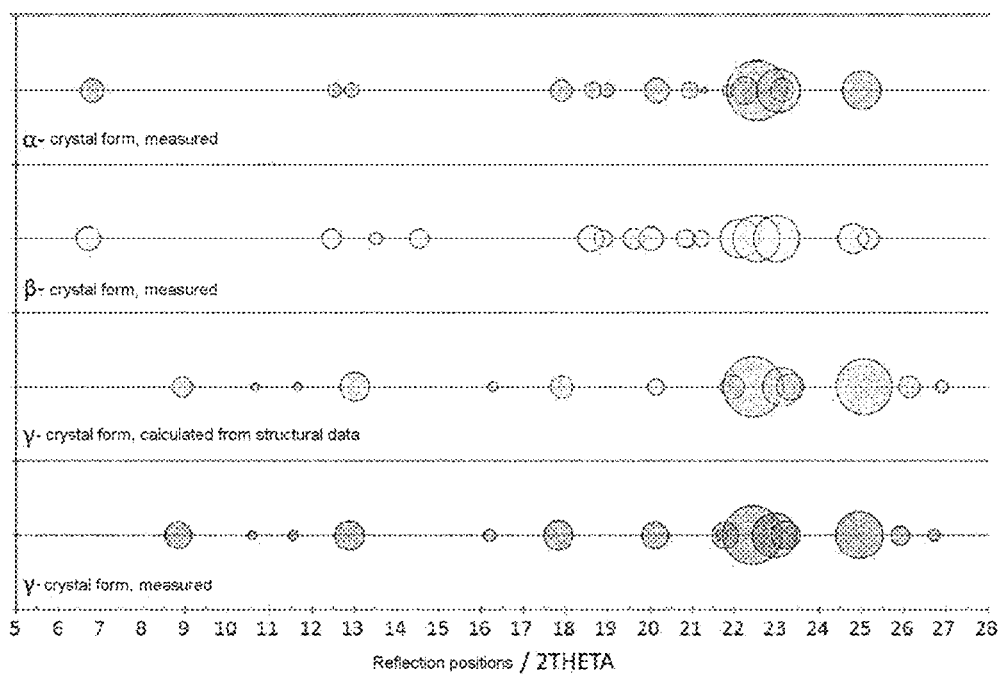
FIG. 10: Reflection positions of crystallisates of the α, β and γ crystal modification and of the calculated γ crystal modification in the powder diffractogram with rel. intensities as bubble diameters.

The powder diffractogram calculated from the structural data of a single-crystal structure analysis of the γ crystal modification by means of PowderCell software (Bundesanstalt für Materialforschung und-prüfung Berlin) is shown in FIG. 6, the characteristic reflections being found in Table 3. The single-crystal X-ray diffractometer IPDS 2T (Stoe) was used for structure determination. A comparison of the reflection positions in FIG. 10 between the calculated and the measured powder diffractogram proves the absence of another crystal modification.

TABLE 3

Characteristic reflections of crystallisates of the γ crystal modification

| γ Crystal modification 2Θ | d | Rel. intensity |
|---|---|---|
| 8.939 | 9.8849 | 33.80% |
| 10.652 | 8.2986 | 12.80% |
| 11.673 | 7.5753 | 13.50% |
| 13.008 | 6.8005 | 48.10% |
| 16.280 | 5.4403 | 16.40% |
| 17.914 | 4.9476 | 37.20% |
| 20.128 | 4.408 | 27.70% |
| 21.768 | 4.0794 | 17.00% |
| 21.960 | 4.0443 | 39.20% |
| 22.432 | 3.9602 | 100.00% |
| 23.113 | 3.845 | 64.40% |
| 23.311 | 3.8128 | 44.90% |
| 25.058 | 3.5508 | 92.60% |
| 26.131 | 3.4704 | 36.00% |
| 26.909 | 3.3107 | 20.50% |

Example 5—Process for the Production of the α Crystal Modification

A starting amount of 24.3 kg of slurry, as detailed in the following table, is placed in a pilot plant having a 10-litre stirred tank reactor and an 11 cm propeller mixer. Seeding is carried out with 2.4 kg % by mass DTPMP crystallisates of the α crystal modification comprising 50% by mass DTPMP, 1.5% by mass chloride and having a main particle size of 20 μm, at a reaction temperature of 30° C. A calculated initial suspension density of 5% by mass is obtained. Precipitation is carried out at a constant stirring speed of 170 rpm.

The suspension density, that is to say the solids content of the suspension in % by mass, is determined gravimetrically via a benchtop centrifuge in 12 ml vials at 6500 rpm/5 minutes. This centrifugation speed of 6500 rpm corresponds to a separating capacity of 3500 g.

After a test duration of 15.5 hours, the solid is separated from the liquid via a porcelain suction filter (50 mbar, on filter paper), the unwashed solid and the filtrate having the contents of DTPMP, chloride and ortho-phosphate indicated in the following table.

|  | Amount [kg] | DTPMP content [% by mass] | Chloride content [% by mass] | Chloride fraction in DTPMP [% by mass] | Ortho-phosphate content [% by mass] |
|---|---|---|---|---|---|
| Slurry | 24.3 | 46.5 | 3.3 | 7.1 | 0.6 |
| Solid unwashed | 8.5 | 59.5 | 2.6 | 4.4 | 0.4 |
| Filtrate: | 15.8 | 32.8 | 3.8 | 11.6 | 0.5 |

As the suspension density increases, the thin crystal plates increasingly rub together and are thereby destroyed mechanically. This leads to new nuclei, so that the suspension density increases further as they heal. As a result, no further significant crystal growth is observed, but the crystals remain at crystal sizes of about 20 μm. These small crystal sizes, combined with the plate form typical for crystal form A, result in high specific surface areas. This leads to extremely high residual moisture contents and losses due to washing.

Figure 3:
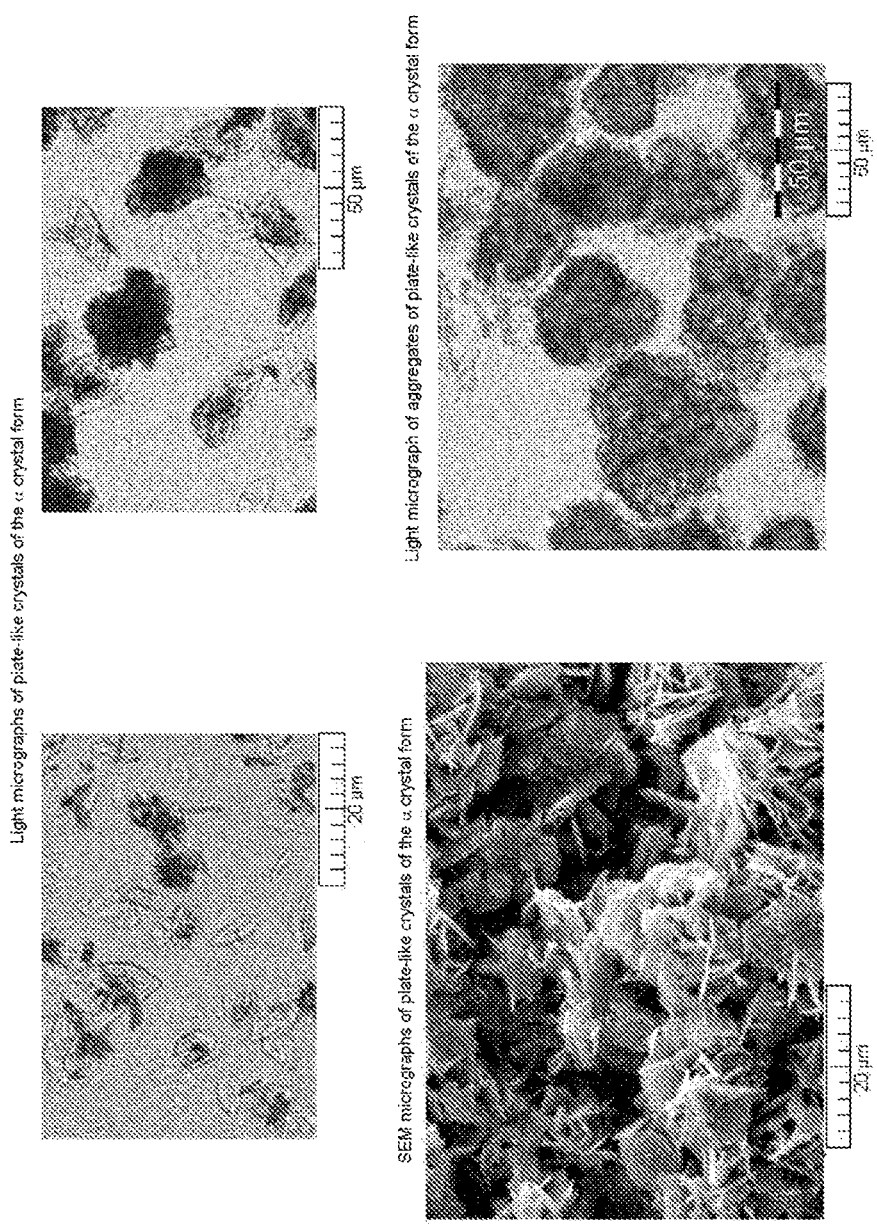
FIG. 3: top: light micrograph of plate-like crystallisates of the α crystal modification; bottom: SEM micrographs thereof.

The grain growth to be observed by means of laser diffraction on a macroscopic scale takes place primarily via the formation of agglomerates (see FIG. 3, bottom right image), which are visible by means of a scanning electron microscope. Although the agglomeration has a favourable effect on the sedimentation behaviour and thus also on the filtration behaviour, the inclusion of mother liquor reduces the purification effect.

A two-step process appears to be expedient here. The solid precipitated and separated off by filtration in the first step is dissolved again, without being washed, and recrystallised in a second step in a mother liquor which is now purer and, on account of its higher purity, advantageously less supersaturated. After filtration, this solid is washed and shows significantly better purification. However, the high content of residual moisture of >60% by mass disadvantageously remains. Should this material be dried energy-efficiently at temperatures >60° C., it forms aggregates by rolling up or even begins to dissolve in the residual moisture. In order to counteract this, it is necessary to carry out drying beforehand to residual moisture contents <40% by mass with significantly lower energy inputs, that is to say at temperatures of about 40° C.

This dependency is shown by the following example for determining the drying behaviour of crystallisates in dependence on residual moisture and product purity.

A DTPMP solid isolated by recrystallisation is characterised by residues of adhering mother liquor via the quality parameters listed in the following table. Determination of the residual moisture content by means of a halogen dryer HB 43 S/Mettler Toledo is carried out isothermally at the indicated temperature using the shutoff criterion 4 (AK4=mean weight loss is <1 mg per 90 seconds):

|  | DTPMP [% by mass] | Chloride [% by mass] | PO4 inorg. [% by mass] | H3PO3 [% by mass] | Residual moisture 130° C. AK4 |
|---|---|---|---|---|---|
| unwashed sample | 47.7 | 1.8 | 0.13 | 3 | 45.6 |

After a purification step, which consists in suspending the solid in water and then separating it off by means of a filtering centrifuge, the following quality criteria are obtained:

|  | DTPMP [% by mass] | Chloride [% by mass] | PO4 inorg. [% by mass] | H3PO3 [% by mass] | Residual moisture 130° C. AK4 |
|---|---|---|---|---|---|
| washed sample | 50.9 | 0.7 | 0.15 | 1.5 | 44.8 |

The adhering residual moisture is removed stepwise from these solid samples in a rotary evaporator at 40° C. and 5 mbar vacuum, so that a series of samples with decreasing residual moisture content is prepared from each of the two purity grades (unwashed and washed).

| Unwashed sample no. | Residual moisture [% by mass] | Washed sample no. | Residual moisture [% by mass] |
|---|---|---|---|
| 1 | 53 | 1 | 51 |
| 2 | 47 | 2 | 47 |
| 3 | 36 | 3 | 40 |
| 4 | 32 | 4 | 36 |
| 5 | 26 | 5 | 31 |
| 6 | 14 | 6 | 24 |
| 7 | 11 | 7 | 19 |

Figure 12:
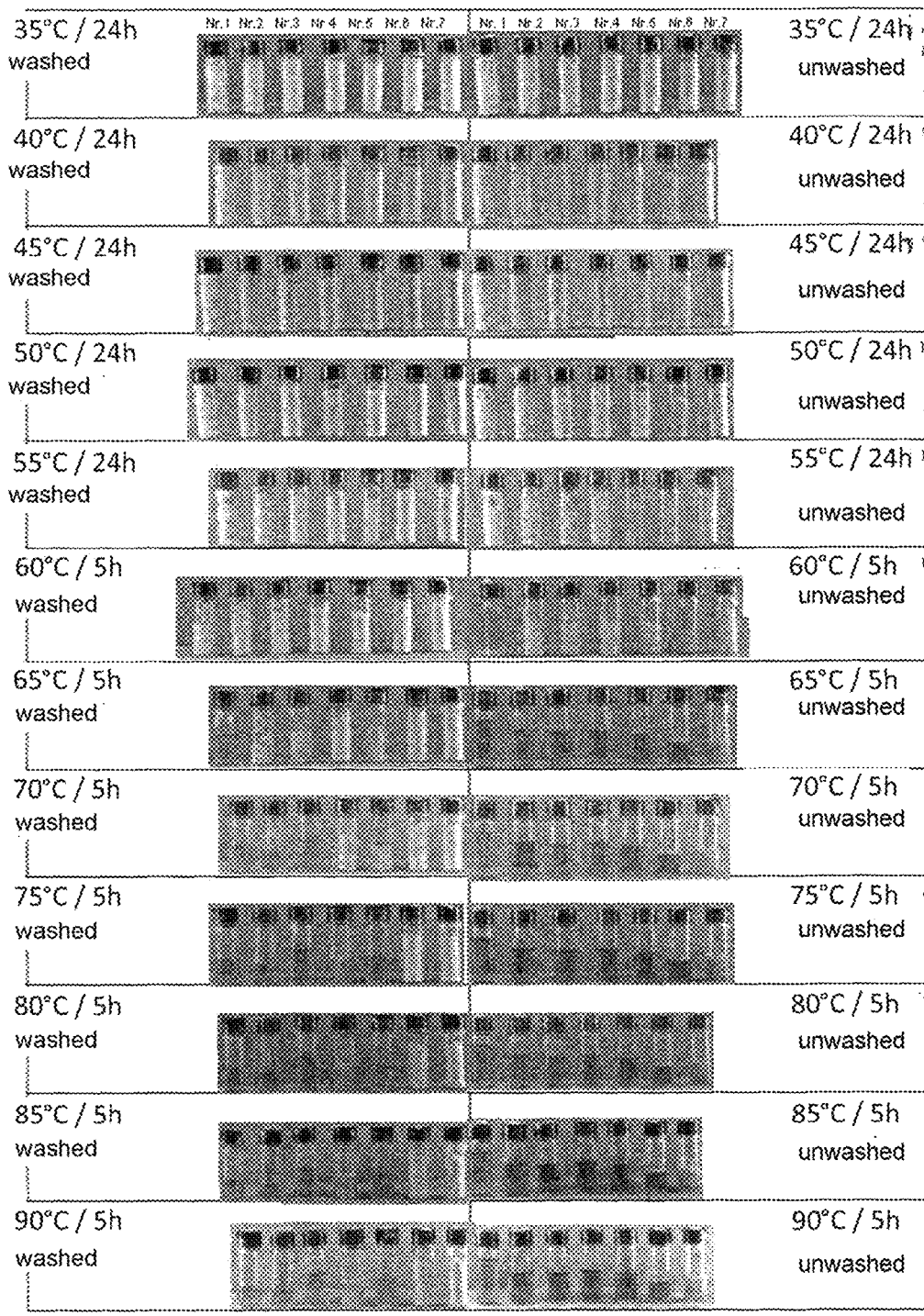
FIG. 12: Drying behaviour of crystallisates in dependence on purity and residual moisture.
Figure 13:
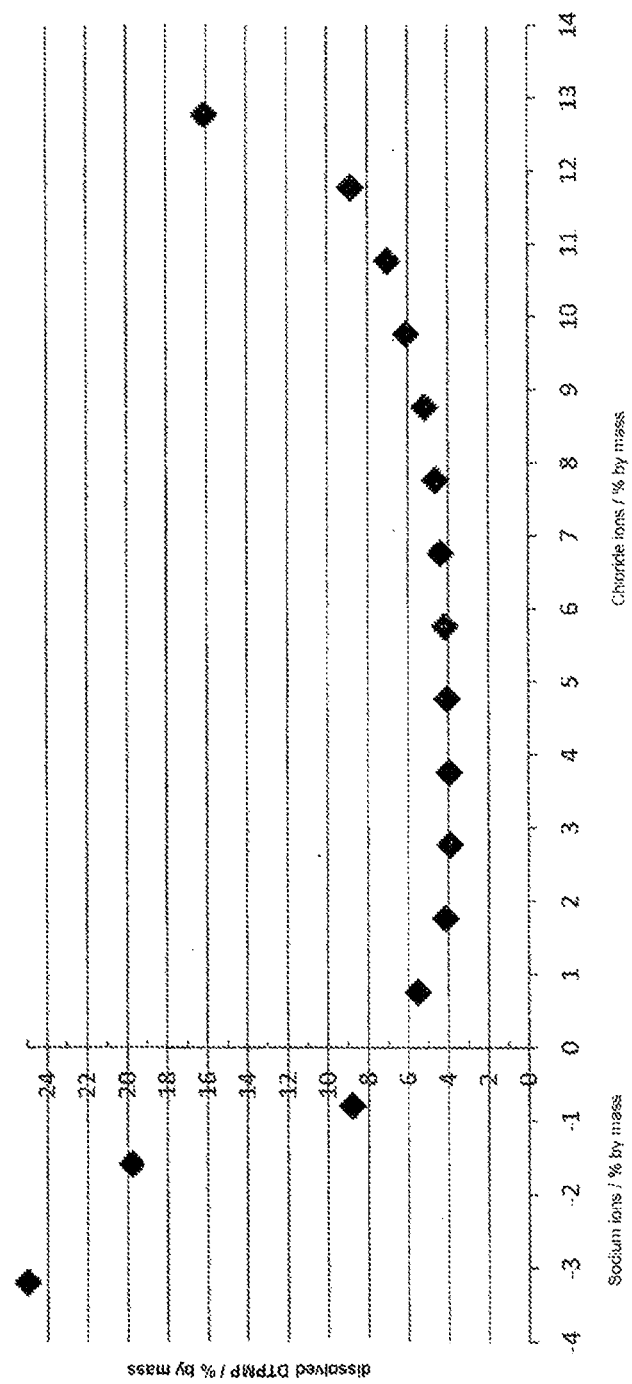
FIG. 13: Solubility of DTPMP at room temperature in dependence on the concentration of sodium ions and chloride ions in % by mass.

4 ml borosilicate vials are filled with this sample material and the filling level is adjusted to ⅔ of the height of the glass by gentle tapping. In order to minimise evaporative losses, the screw cap of each vial is additionally sealed with a polyethylene film. All the samples are shaken in parallel in a tempering block on a heating and cooling shaker ThermoTwister comfort/Quantifoil Instruments GmbH for a defined period at a defined temperature and then assessed visually. Classification is made according to the following points system:

5 points=sample unchanged
4 points=sample compacted/started to dissolve
3 points=sample visibly started to dissolve
2 points=sample cloudy highly viscous solution
1 point=sample dissolved to clear solution The following two tables compile the observations made at the end of each tempering step, photographs (see FIG. 12) complete the overview.

Table of samples of unwashed quality:

| Test duration [h] | 24 | 24 | 24 | 24 | 24 | 24 | 5 | 5 | 5 | 5 | 5 | 5 |
|---|---|---|---|---|---|---|---|---|---|---|---|---|
| Temperature [° C.] | 35 | 40 | 45 | 50 | 55 | 60 | 65 | 70 | 75 | 80 | 85 | 90 |
| 51 [% by mass] residual moisture | 5 | 5 | 5 | 5 | 5 | 2 | 1 | 1 | 1 | 1 | 1 | 1 |
| 47 [% by mass] residual moisture | 5 | 5 | 5 | 5 | 5 | 3 | 1 | 1 | 1 | 1 | 1 | 1 |
| 40 [% by mass] residual moisture | 5 | 5 | 5 | 5 | 5 | 3 | 1 | 1 | 1 | 1 | 1 | 1 |
| 36 [% by mass] residual moisture | 5 | 5 | 5 | 5 | 5 | 3 | 1 | 1 | 1 | 1 | 1 | 1 |
| 31 [% by mass] residual moisture | 5 | 5 | 5 | 5 | 4 | 3 | 1 | 1 | 1 | 1 | 1 | 1 |
| 24 [% by mass] residual moisture | 5 | 5 | 5 | 4 | 4 | 3 | 2 | 1 | 1 | 1 | 1 | 1 |
| 19 [% by mass] residual moisture | 5 | 5 | 5 | 5 | 5 | 4 | 2 | 2 | 2 | 2 | 2 | 2 |

Table of samples of "washed quality":

| Test duration [h] | 24 | 24 | 24 | 24 | 24 | 24 | 5 | 5 | 5 | 5 | 5 | 5 |
|---|---|---|---|---|---|---|---|---|---|---|---|---|
| Temperature [° C.] | 35 | 40 | 45 | 50 | 55 | 60 | 65 | 70 | 75 | 80 | 85 | 90 |
| 53 [% by mass] residual moisture | 5 | 5 | 5 | 5 | 5 | 3 | 1 | 1 | 1 | 1 | 1 | 1 |
| 47 [% by mass] residual moisture | 5 | 5 | 5 | 5 | 5 | 5 | 3 | 1 | 1 | 1 | 1 | 1 |
| 36 [% by mass] residual moisture | 5 | 5 | 5 | 5 | 5 | 5 | 3 | 1 | 1 | 1 | 1 | 1 |
| 32 [% by mass] residual moisture | 5 | 5 | 5 | 5 | 5 | 5 | 4 | 3 | 3 | 2 | 2 | 2 |
| 26 [% by mass] residual moisture | 5 | 5 | 5 | 5 | 4 | 5 | 4 | 3 | 3 | 2 | 2 | 2 |
| 14 [% by mass] residual moisture | 5 | 5 | 5 | 5 | 5 | 5 | 5 | 5 | 5 | 5 | 5 | 5 |
| 11 [% by mass] residual moisture | 5 | 5 | 5 | 5 | 5 | 5 | 5 | 5 | 5 | 5 | 5 | 5 |

The photographs of the samples taken at the end of each tempering step show very clearly that samples with high residual moisture contents and at the same time low purity compact at only low temperatures and dissolve partially or even completely in their own residual moisture. This property makes economical process management, that is to say high production yields by the input of a large amount of drying energy, significantly more difficult. DTPMP solid qualities with less than 0.7% chloride and less than 40% residual moisture, on the other hand, are found to be advantageous in terms of their drying behaviour.

Figure 2:
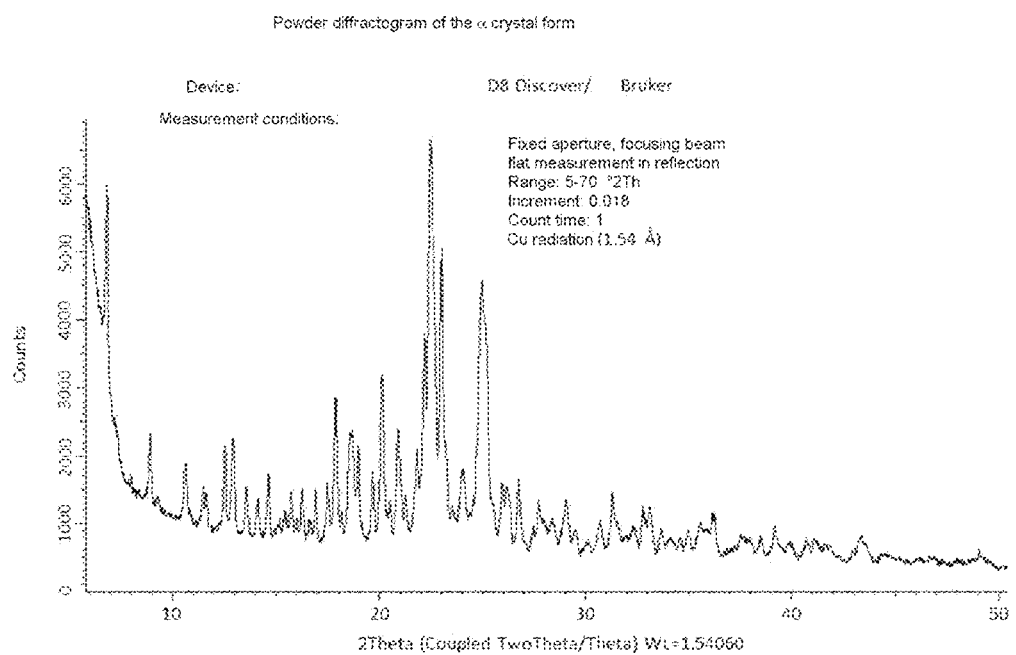
FIG. 2: powder diffractogram of crystallisates of the α crystal modification.

The X-ray diffraction diagram, recorded with Cu-K$_\alpha$1 radiation, of the α crystal modification according to the invention is shown in FIG. 2, the characteristic reflections being found in Table 1, and proves the absence of another crystal modification. The high-resolution X-ray diffractometer D8 Discover (Bruker) was used to record the X-ray diffraction diagram.

TABLE 1

Characteristic reflections of crystallisates of the α crystal modification

| 2Θ | d | Rel. intensity |
|---|---|---|
| 6.796 | 12.99626 | 38.00% |
| 12.534 | 7.05661 | 21.70% |
| 12.937 | 6.83779 | 24.10% |
| 17.9 | 4.9513 | 35.60% |
| 18.641 | 4.75618 | 26.50% |
| 18.981 | 4.67183 | 22.00% |
| 20.152 | 4.40287 | 41.00% |
| 20.94 | 4.23896 | 27.60% |
| 21.276 | 4.17267 | 10.20% |
| 21.854 | 4.06371 | 21.30% |
| 22.229 | 3.99591 | 45.80% |
| 22.52 | 3.94501 | 100.00% |
| 23.031 | 3.85863 | 72.60% |
| 23.119 | 3.84415 | 39.10% |
| 25 | 3.55902 | 64.30% |

Example 6—Process for the Production of the β Crystal Modification

A starting amount of 4.49 kg of slurry, containing 38.9% by mass DTPMP and 3.0% by mass chloride, is placed in a double-walled 5-litre stirred tank reactor having a 14 cm anchor agitator. Seeding was carried out once with 0.2 kg of crystallisate of the β crystal modification comprising 85% by mass DTPMP and 0.1% by mass chloride and having a main particle size of 30 μm. A calculated initial suspension density of 3.6% by mass was obtained. Precipitation took place at a constant stirring speed of 150 rpm.

The process is left isothermal for a period of 3 days. The crystallisation is first left at a constant initial temperature of 58° C. for 24 hours and then the temperature is lowered continuously to 46° C. with a temperature profile of about 1 K per 6 hours and left for a remaining period of 71 hours. The matured crystallisate is separated from the aqueous solution in a filtering centrifuge having a perforated drum with a filtering area of 235 cm$^2$ and at a centrifugation speed of 6800 rpm for 2 minutes. This centrifugation speed of 6800 rpm corresponds to a separating capacity of 3500 g. Three washing operations with washing water (corresponding to half the amount of solid, divided into 3 equal amounts) are then carried out. Finally, the separated crystallisate is dried for 5 minutes at a centrifugation speed of 10,000 rpm. This centrifugation speed of 10,000 rpm corresponds to a separating capacity of 8400 g.

| | Amount [g] | DTPMP [% by weight] | Chloride [% by weight] | Chloride in DTPMP [% by weight] |
|---|---|---|---|---|
| Slurry | 4492 | 38.9 | 3.0 | 7.7 |
| Solid unwashed | 1509 | 83.6 | 0.6 | 0.7 |
| Solid washed 1x | | 85.4 | 0.36 | 0.4 |
| Solid washed 2x | | 86.0 | 0.3 | 0.4 |
| Solid washed 3x | 1017 | 87.2 | 0.09 | 0.1 |
| Filtrate: | 2915 | 26.9 | 3.8 | 14.1 |
| Washing water: | 1312 | 12.1 | 1.54 | 12.7 |

The particle size of the DTPMP crystallisates is then determined by means of a laser diffraction particle size analyser LS 13 320/Beckmann Coulter at a wavelength of 780 nm.

| | End |
|---|---|
| $d_{50}$ [μm] | 60 |
| $d_{10}$ [μm] | 17 |
| $d_{90}$ [μm] | 113 |

The determination of the average particle size at the end of the test is carried out by means of a microscope and Olympus visualisation software (cf. FIG. 5):

| Length [μm] | 50-120 |
|---|---|
| Width [μm] | 10-50 |
| Thickness [μm] | 1-5 |

Crystallisates of the β crystal modification can be obtained with comparable yields and degrees of purification over a wide temperature range. Cooling crystallisation requires low cooling rates in order to avoid supersaturation. An isothermal reduction of supersaturation is possible both in the upper existence range of the β crystal modification and in the lower existence range of the β crystal modification.

Figure 4:
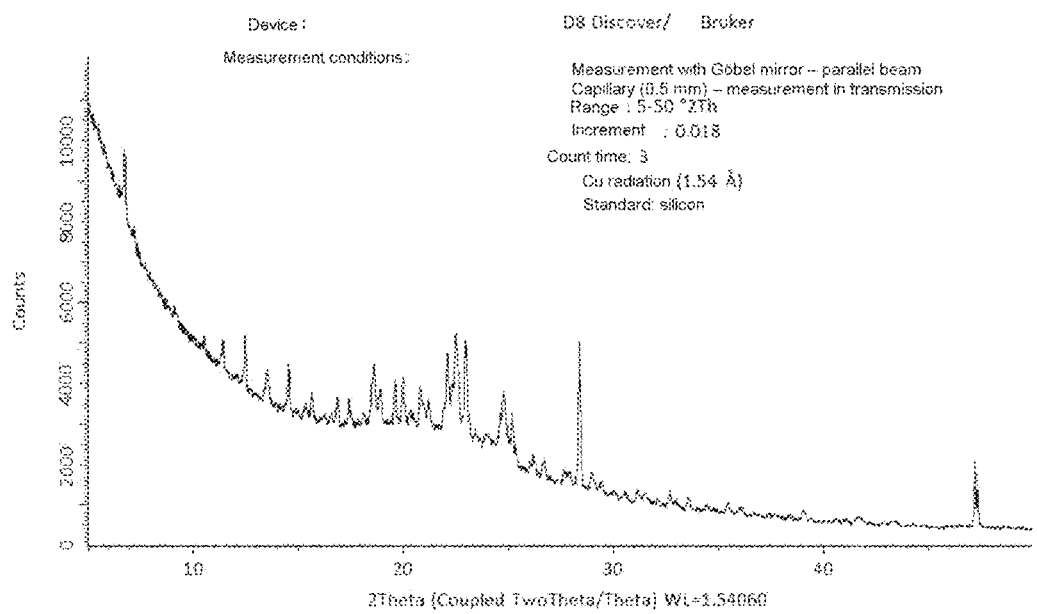
FIG. 4: powder diffractogram of crystallisates of the β crystal modification.

The X-ray diffraction diagram, recorded with Cu-K$_\alpha$1 radiation, of the β crystal modification according to the invention is shown in FIG. 4, the characteristic reflections being found in Table 2, and proves the absence of another crystal modification. The high-resolution X-ray diffractometer D8 Discover (Bruker) was used to record the X-ray diffraction diagram.

TABLE 2

Characteristic reflections of crystallisates of the β crystal modification

| 2Θ | d | Rel. intensity |
|---|---|---|
| 6.707 | 13.1694 | 41.30% |
| 12.464 | 7.09618 | 33.30% |
| 13.512 | 6.54779 | 22.10% |
| 14.553 | 6.08179 | 32.50% |
| 18.596 | 4.76749 | 43.80% |
| 18.894 | 4.69305 | 29.40% |
| 19.614 | 4.52231 | 36.50% |
| 20.02 | 4.43159 | 39.80% |
| 20.854 | 4.25612 | 32.00% |
| 21.204 | 4.18675 | 27.70% |
| 22.12 | 4.01534 | 65.10% |
| 22.522 | 3.94466 | 79.10% |
| 22.988 | 3.86569 | 76.80% |
| 24.8 | 3.58726 | 50.60% |
| 25.166 | 3.53581 | 35.70% |

Example 7—Thermal Analysis of the Crystals

Figure 11:
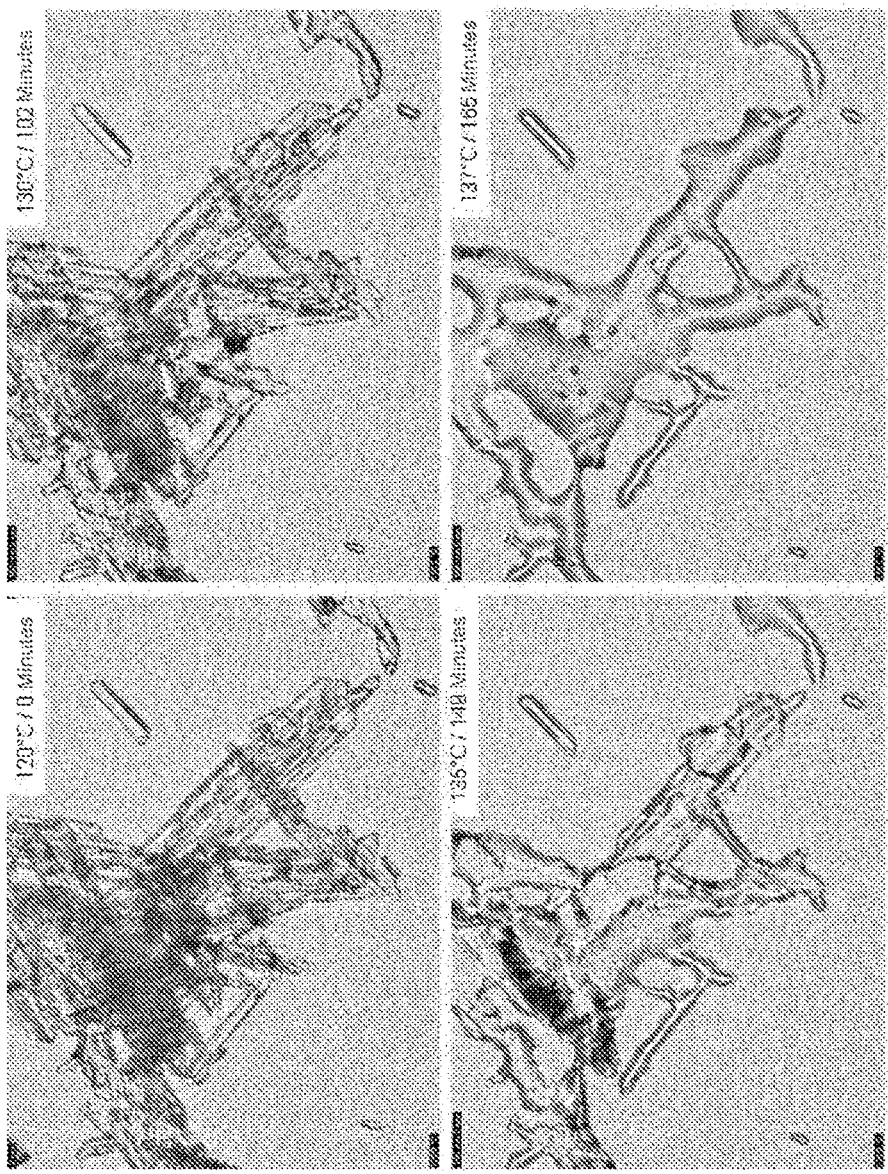
FIG. 11: Thermo-optical analysis of the β crystal modification; heating regime: 120-140° C. heating rate 0.1 K/minute; hot stage: FP82HT hot stage/Mettler Toledo, software analySIS DOCU/Olympus Soft Imaging GmbH.

In a drying cabinet, crystallisates of the α, β and γ crystal modification are pre-dried at 80° C. for 24 hours to residual moisture contents of <10% by mass. Thermogravimetric analysis is carried out by placing the samples in a platinum crucible under a heating regime of 30° C. to 230° C. with a constant heating rate of 1.0 K/min in a TG/DTA 220 (Seiko Instruments). Melting of the samples in a temperature range between 130 and 140° C. is detectable thermooptically (FIG. 11), the beginning of melting of crystallisates of the α crystal modification lying at 130° C., the β crystal modification melting at 135° C., and melting beginning at 140° C. for crystallisates of the γ crystal modification. The γ crystal modification can thus advantageously be dried with higher energy inputs and thus more energy efficiently than crystallisates of the α or β crystal modification, while retaining the solid state of aggregation.

Figure 9:
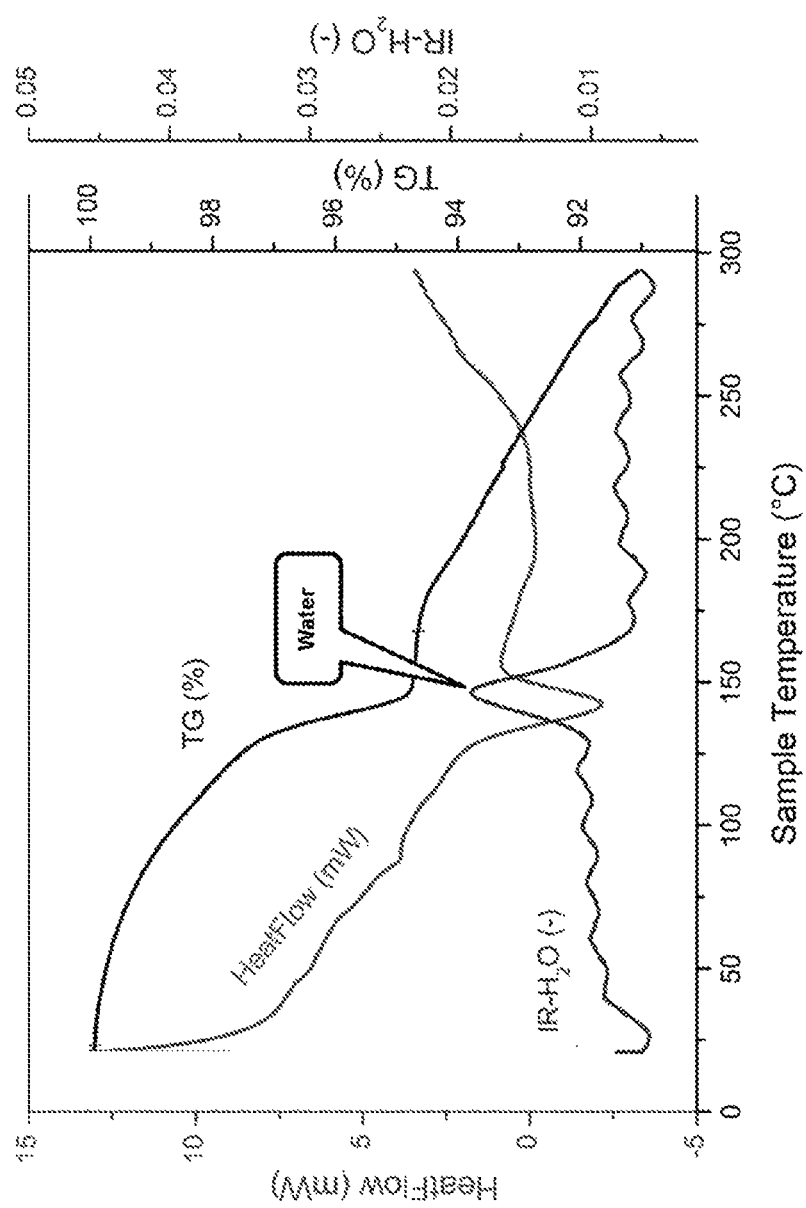
FIG. 9: DSC/TG coupled IR gas analysis for determining the water content of DTPMP crystallisates.

By means of DSC/TG coupled IR gas analysis (FIG. 9), the loss of mass of 3 to 5% by mass which occurs upon melting can be attributed to water. This amount of water corresponds to a substance amount of 1 mol of water per mol of DTPMP, plus a negligible amount of retained water of residual moisture attached to the surface. The analysis is the proof that a crystallisate of DTPMP is present in the form of the crystalline monohydrate of the acid DTPMP.

Example 8—Determination of the Hygroscopicity

Figure 14:
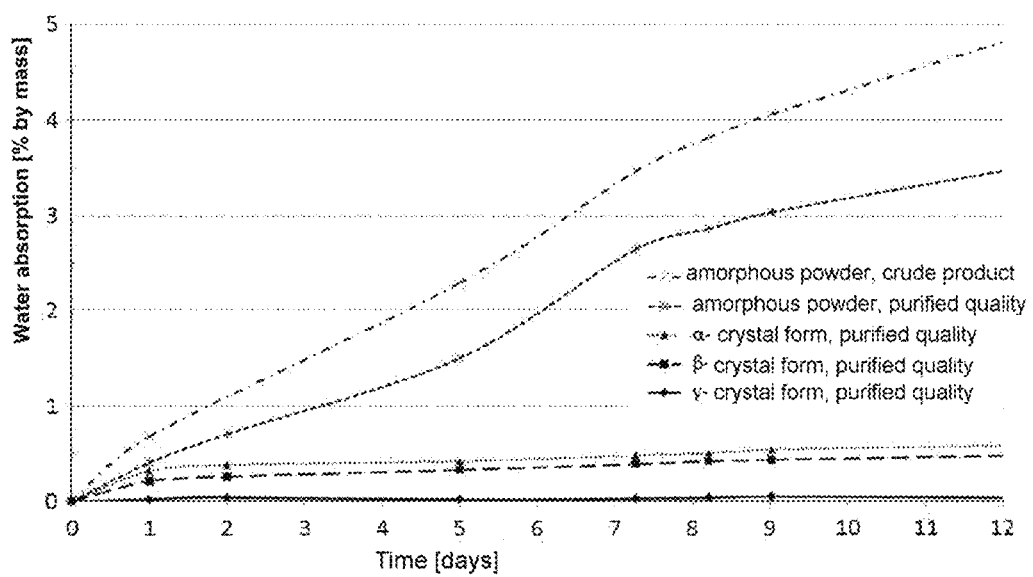
FIG. 14: Water absorption capacity of the crystallisates according to the invention in comparison with amorphous DTPMP solids of different qualities.

In order to determine the hygroscopicity, solid samples were stored in 25 ml glass beakers in a desiccator under constant humidity. Via a saturated magnesium nitrate solution with precipitate (about ⅓ precipitate in ⅔ of the solution), a relative humidity of 55% by mass becomes established at 22±2° C. The water absorption of the samples was determined gravimetrically once daily over a period of 12 days as the difference in mass (see FIG. 14).

Two spray-dried powders were tested as comparison with crystallisate samples of the crystallisates of the α, β and γ crystal modification.

A DTPMP synthesis product having the quality parameters from Table 4 used as the starting slurry for the crystallisation was spray dried with a Büchi-Mini Spray Dryer B-290.

The second spray-dried powder was obtained from re-dissolved crystallisate of the α crystal modification and thus showed the same low degree of impurity as the crystallisate of the α crystal modification.

The composition of the samples used and the relative water absorption [in % by mass] are to be found in Table 4 below.

| Product | Sum (H3PO4 + H3PO3)/ DTPMP % by mass | Chloride/ DTPMP % by mass | Bulk density [g/ml] | Relative water absorption % by mass/day |
|---|---|---|---|---|
| amorphous powder from spray drying of an unpurified DTPMP synthesis product | 6.5 | 3.5 | 0.27 | 0.40 |
| amorphous powder from spray drying of a DTPMP acid purified by recrystallisation | 3.3 | 1.3 | 0.27 | 0.29 |

-continued

| Product | Sum (H3PO4 + H3PO3)/ DTPMP % by mass | Chloride/ DTPMP % by mass | Bulk density [g/ml] | Relative water absorption % by mass/day |
|---|---|---|---|---|
| Crystal form α, purified quality | 3.3 | 1.3 | 0.36 | 0.03 |
| Crystal form β, purified quality | 1.1 | 0.3 | 0.49 | 0.04 |
| Crystal form γ, purified quality | 0.95 | 0.05 | 0.59 | 0.003 |

A clear differentiation is possible after only a short time. Spray-dried powders of the unpurified DTPMP synthesis product (amorphous structure) exhibit the greatest hygroscopicity. The DTPMP quality purified by recrystallisation and spray dried (amorphous structure) exhibits a lower water absorption capacity than the unpurified crude product while having the same very high specific surface area.

By contrast, the crystallisates of crystal modification α, β or γ according to the invention are distinguished by consistently low water absorption, crystal form γ exhibiting by far the lowest hygroscopicity. This appears to be due to the compact, cuboid crystal form, which results in a high purification success and low hygroscopicity.

Example 9—Hygroscopicity of Acid and Salts

Figure 15:
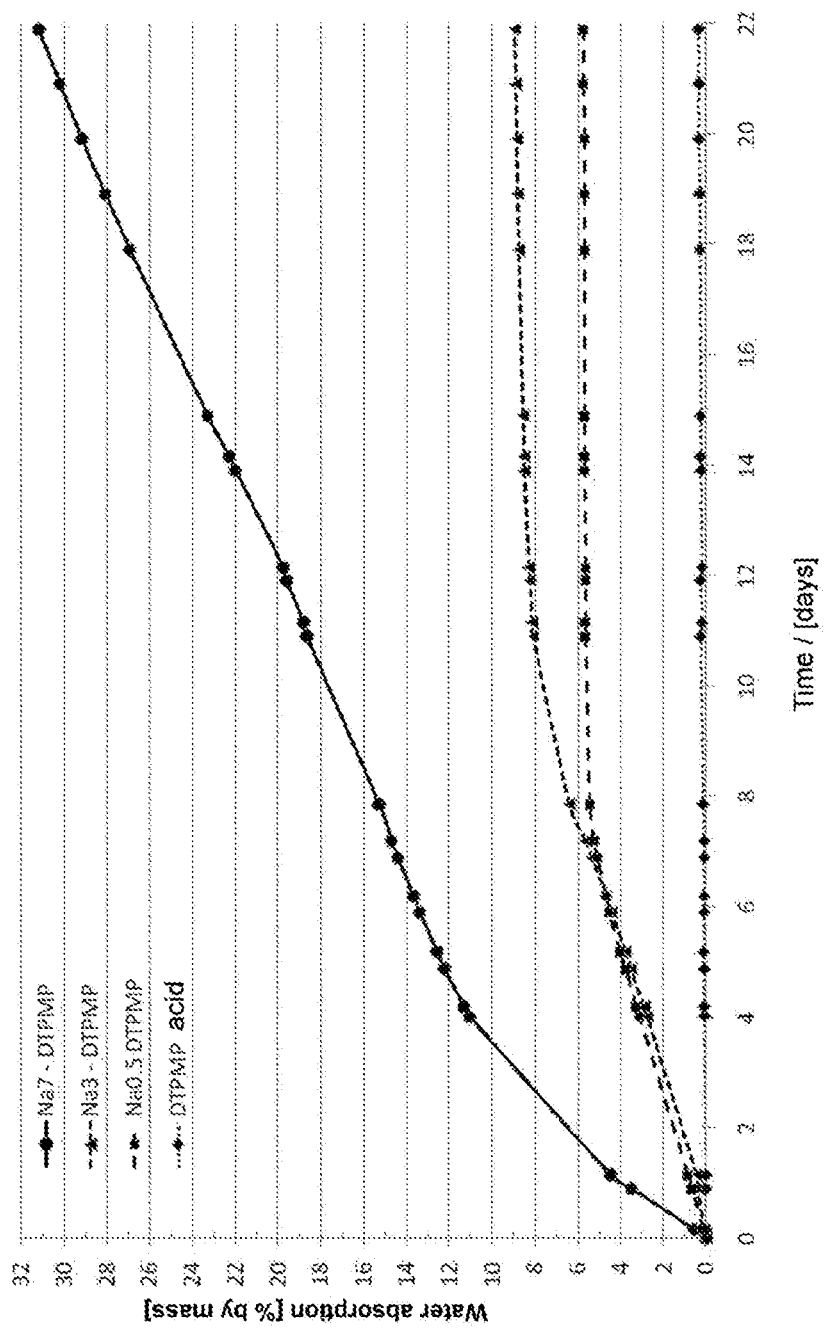
FIG. 15: Water absorption capacity of purified DTPMP acid in comparison with the sodium salts thereof (Na$_7$-DTPMP, Na$_3$-DTPMP, Na$_{0.5}$DTPMP).

In a further test, the influence of the degree of neutralisation of the phosphonic acid DTPMP on the hygroscopicity was studied, on account of its industrial relevance, especially the sodium salts. To that end, 10 g of sample were stored in four crystallisation dishes of equal size in a desiccator under constant humidity. Via a saturated magnesium nitrate solution with precipitate (about ⅓ precipitate in ⅔ of the solution), about 55% by weight humidity is established at 22° C. The water absorption of the samples was determined gravimetrically twice daily over a period of 22 days as the difference in mass (see FIG. 15).

A crystallisate of the α crystal modification with a foreign acid content of 3.8% by weight chloride and in total 6.6% by weight $H_3PO_4$ and $H_3PO_3$ per 100% by mass DTPMP was dissolved again. Portions were neutralised with sodium hydroxide solution to pH (1% strength)=1.7 for the $Na_{0.5}$-DTPMP salt, pH (1% strength)=2.1 for the $Na_3$-DTPMP salt and pH (1% strength)=6.6 for the $Na_7$-DTPMP salt. These aqueous solutions were spray dried using a Büchi-Mini Spray Dryer B-290.

After only half the test time, the powder samples neutralised to pH 7 are visibly contracting to form a block. After 22 days, the powdered structure of the DTPMP acid is still recognisable, the sample of the $Na_7$ salt has liquefied.

This shows that, with the same, low degree of impurity, solids of DTPMP acid are stable to storage, while this is not the case for the sodium salts of DTPMP.

What is claimed is:

1. Crystallisate of the pure acid diethylenetriamine penta (methylenephosphonic acid) (DTPMP) of the general formula (I) or a tautomeric form thereof:

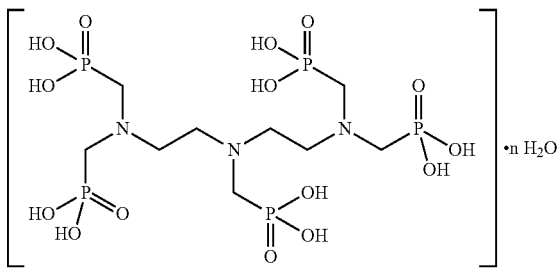

(I)

wherein n is a number between 0 and 2, and
wherein the crystallisate has at least one crystal modification selected from α, β and γ,
wherein the α crystal modification comprises the following characteristic reflections in the X-ray diffraction diagram, measured with Cu-K$_\alpha$ radiation:

| 2Θ | d |
|---|---|
| 6.8 | 13.00 |
| 17.9 | 5.0 |
| 20.2 | 4.40 |
| 22.2 | 4.00 |
| 22.5 | 3.95 |
| 23.0 | 3.86 |
| 23.1 | 3.84 |
| 25.0 | 3.6. | wherein the β crystal modification comprises the following characteristic reflections in the X-ray diffraction diagram, measured with Cu-K$_\alpha$ radiation:

| 2Θ | d |
|---|---|
| 6.7 | 13.17 |
| 18.6 | 4.77 |
| 19.6 | 4.5 |
| 20.0 | 4.4 |
| 22.1 | 4.0 |
| 22.5 | 3.9 |
| 23.0 | 3.9 |
| 24.8 | 3.6 |
| 25.2 | 3.5, | and
wherein the γ crystal modification comprises the following characteristic reflections in the X-ray diffraction diagram, measured with Cu-K$_\alpha$ radiation:

| 2Θ | d |
|---|---|
| 13.0 | 6.8 |
| 17.9 | 4.9 |
| 22.0 | 4.0 |
| 22.4 | 4.0 |
| 23.1 | 3.8 |
| 23.3 | 3.8 |
| 25.1 | 3.6 |
| 26.1 | 3.4. |

2. A process for obtaining solid crystalline diethylenetriamine penta(methylenephosphonic acid) (DTPMP) as the pure acid of the general formula (I) according to claim 1 or a tautomeric form thereof from an aqueous crude product containing DTPMP at a pH of less than 4, comprising the following steps:
   a. introducing seed crystals comprising DTPMP into an aqueous crude product containing DTPMP with a total fraction in the range of from 10 to 65% by mass, up to a suspension density in the range of from 1 to 25%,
   b. inputting kinetic energy into the aqueous crude product, whereby a crystallisate containing DTPMP as the pure acid in a total content of at least 75% by mass precipitates, and
   c. separating the crystallisate from the aqueous crude product by sedimentation and/or filtration.

3. The process according to claim 2, wherein the aqueous crude product contains impurities in the form of secondary products and/or unreacted educts.

4. The process according to claim 2, wherein the input of kinetic energy takes place in the form of stirring and/or shaking and/or ultrasound treatment.

5. The process according to claim 2, wherein the aqueous crude product for the obtainment of solid has a temperature in the range of from 25 to 85° C.

6. The process according to claim 2, wherein a separated crystallisate has a content of dry matter of at least 65%.

7. The process according to claim 2, wherein the process comprises at least one isothermal process stage in which the temperature difference in the aqueous crude product is constant over a defined period of the input of kinetic energy.

8. The process according to claim 7, wherein the temperature of the aqueous crude product is reduced with a temperature profile of from 1 to 7 K per day between the defined period of two isothermal process stages.

9. The process according to claim 2, wherein the process is completed in a quasi-continuous operation.

10. The process according to claim 2, wherein the aqueous crude product for the obtainment of solid comprises a strong acid in the range of from 1 to 4.5% by mass.

11. A method for purifying a water-containing crude product containing diethylenetriamine penta(methylenephosphonic acid) (DTPMP) in a total content of at least 10% by mass, said method comprising performing the processing according to claim 2 in order to purify said water-containing crude product containing DTPMP in a total content of at least 10% by mass.

* * * * *